United States Patent
Bhattacharyya et al.

(10) Patent No.: US 10,527,953 B2
(45) Date of Patent: Jan. 7, 2020

(54) METROLOGY RECIPE SELECTION

(71) Applicant: ASML NETHERLANDS B.V., Veldhoven (NL)

(72) Inventors: Kaustuve Bhattacharyya, Veldhoven (NL); Arie Jeffrey Den Boef, Waalre (NL); Martin Jacobus Johan Jak, 's-Hertogenboşch (NL)

(73) Assignee: ASML Netherlands B.V., Veldhoven (NL)

( * ) Notice: Subject to any disclaimer, the term of this patent is extended or adjusted under 35 U.S.C. 154(b) by 148 days.

(21) Appl. No.: 15/706,625

(22) Filed: Sep. 15, 2017

(65) Prior Publication Data

US 2018/0088470 A1 Mar. 29, 2018

(30) Foreign Application Priority Data

Sep. 27, 2016 (EP) .................................... 16190877
Feb. 23, 2017 (EP) .................................... 17157572

(51) Int. Cl.
| | | |
|---|---|---|
| *G03F 7/20* | (2006.01) | |
| *G01B 11/24* | (2006.01) | |
| *G01B 11/30* | (2006.01) | |
| *G01N 21/47* | (2006.01) | |
| *G01N 21/88* | (2006.01) | |

(52) U.S. Cl.
CPC .......... *G03F 7/70633* (2013.01); *G01B 11/24* (2013.01); *G01B 11/30* (2013.01); *G01N 21/47* (2013.01); *G03F 7/705* (2013.01); *G03F 7/70641* (2013.01); *G01N 21/88* (2013.01); *G02F 2202/023* (2013.01)

(58) Field of Classification Search
CPC .. G03F 7/70633; G03F 7/705; G03F 7/70641; G01B 11/24; G01B 11/30; G01N 21/47
USPC .............................. 430/22, 30; 382/145–151
See application file for complete search history.

(56) References Cited

U.S. PATENT DOCUMENTS

| | | |
|---|---|---|
| 7,791,732 B2 | 9/2010 | Den Boef et al. |
| 7,873,504 B1 | 1/2011 | Bevis |
| 8,411,287 B2 | 4/2013 | Smilde et al. |
| 9,081,303 B2 | 7/2015 | Cramer et al. |
| 2006/0066855 A1 | 3/2006 | Den Boef et al. |
| 2008/0094639 A1 | 4/2008 | Widmann et al. |
| 2011/0027704 A1 | 2/2011 | Cramer et al. |
| 2011/0043791 A1 | 2/2011 | Smilde et al. |
| 2012/0242940 A1 | 9/2012 | Nagata et al. |

FOREIGN PATENT DOCUMENTS

| | | |
|---|---|---|
| WO | 2004/066028 | 8/2004 |
| WO | 2009/078708 | 6/2009 |
| WO | 2009/106279 | 9/2009 |
| WO | 2011/012624 | 2/2011 |
| WO | 2013/143814 | 10/2013 |
| WO | 2015/018625 | 2/2015 |
| WO | 2016/083076 | 6/2016 |
| WO | 2016/086056 | 6/2016 |

OTHER PUBLICATIONS

European Search Report and Search Opinion dated May 3, 2017 in corresponding European Patent Application No. 16190877.7.
International Search Report and Written Opinion dated Nov. 9, 2017 in corresponding International Patent Application No. PCT/EP2017/070825.

*Primary Examiner* — Christopher G Young
(74) *Attorney, Agent, or Firm* — Pillsbury Winthrop Shaw Pittman LLP

(57) ABSTRACT

A method including evaluating a plurality of substrate measurement recipes for measurement of a metrology target processed using a patterning process, against stack sensitivity and overlay sensitivity, and selecting one or more substrate measurement recipes from the plurality of substrate measurement recipes that have a value of the stack sensitivity that meets or crosses a threshold and that have a value of the overlay sensitivity within a certain finite range from a maximum or minimum value of the overlay sensitivity.

24 Claims, 15 Drawing Sheets

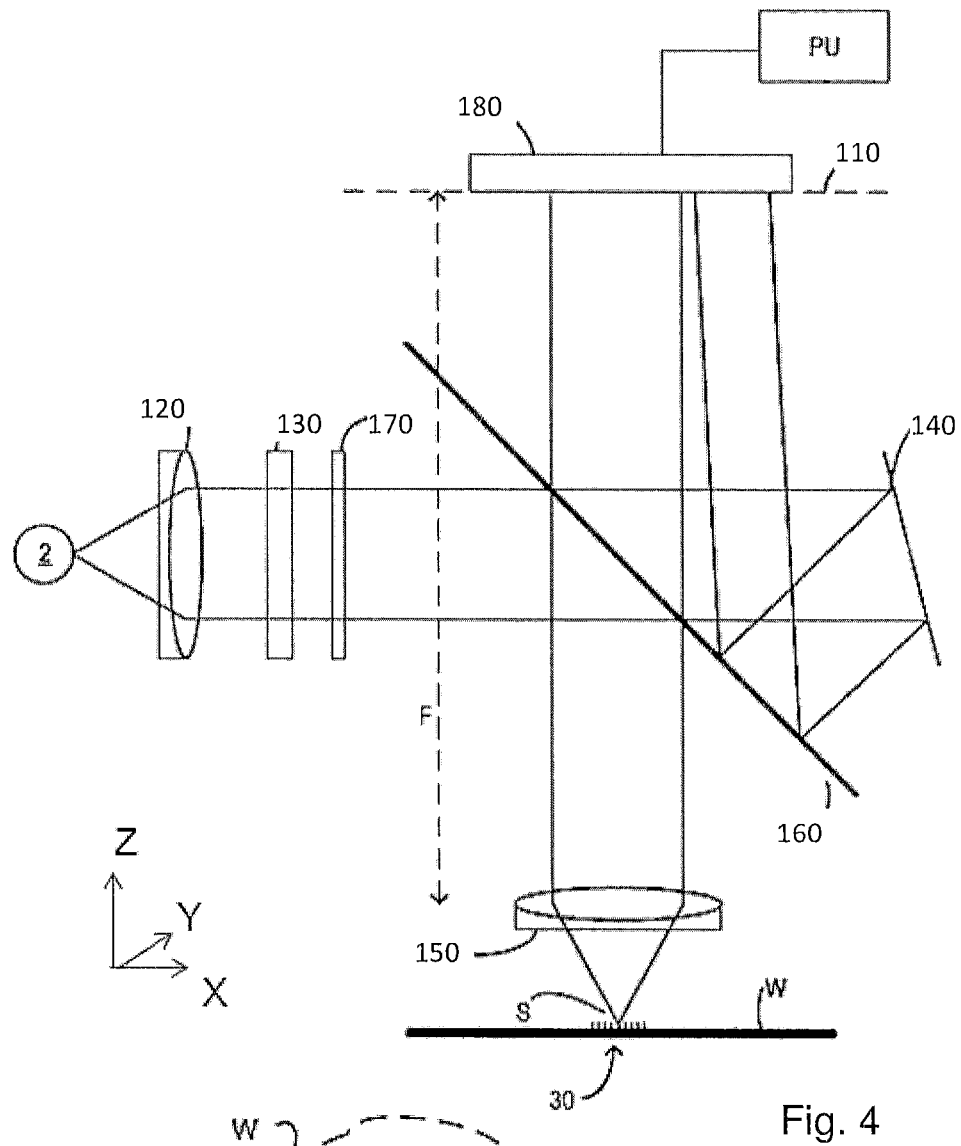
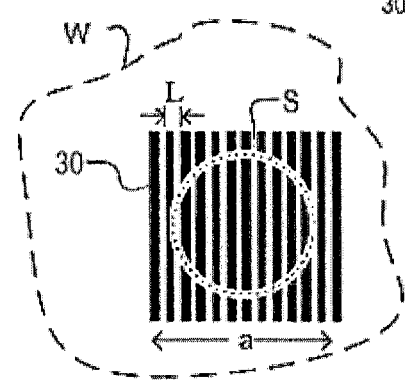
Fig. 4
Fig. 5

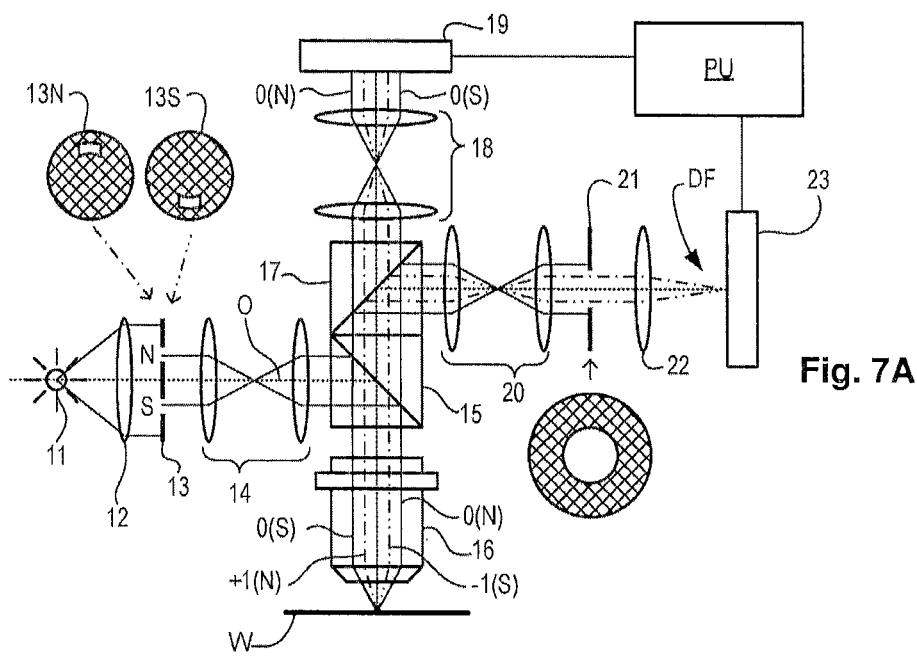
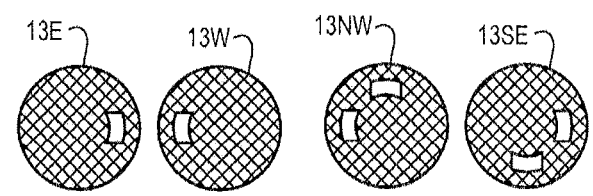
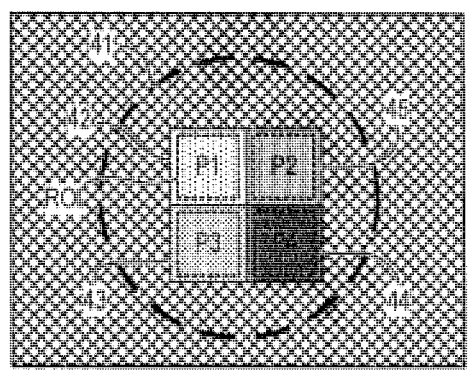
Fig. 7A
Fig. 7B    Fig. 7C    Fig. 7D
Fig. 8    Fig. 9

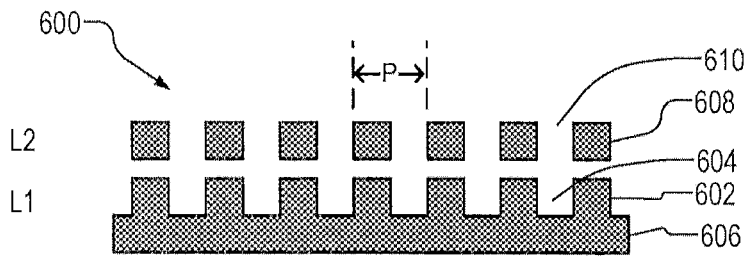
Fig. 11A
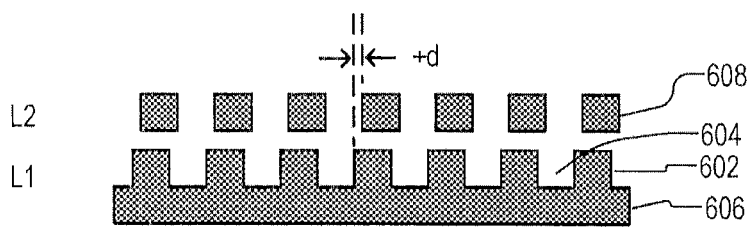
Fig. 11B
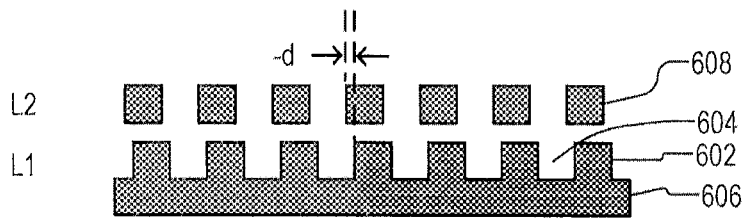
Fig. 11C
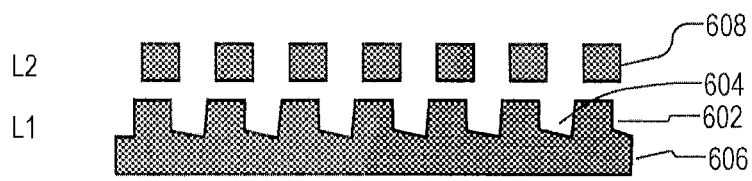
Fig. 11D

METROLOGY RECIPE SELECTION

This application claims the benefit of priority of European patent application no. 16190877.7, filed on Sep. 27, 2016, and of European patent application no. 17157572.3, filed on Feb. 23, 2017. The entire content of each of the foregoing applications is incorporated herein in its entirety by reference.

FIELD

The present disclosure relates to methods and apparatus for inspection (e.g., metrology) usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

Significant aspects to enabling a patterning process (i.e., a process of creating a device or other structure involving patterning (such as lithographic exposure or imprint), which may typically include one or more associated processing steps such as development of resist, etching, etc.) include developing the process itself, setting it up for monitoring and control and then actually monitoring and controlling the process itself. Assuming a configuration of the fundamentals of the patterning process, such as the patterning device pattern(s), the resist type(s), post-lithography process steps (such as the development, etch, etc.), it is desirable to setup the apparatus in the patterning process for transferring the pattern onto the substrates, develop one or more metrology targets to monitor the process, setup up a metrology process to measure the metrology targets and then implement a process of monitoring and/or controlling the process based on measurements.

So, in a patterning process, it is desirable to determine (e.g., measure, simulate using one or more models that model one or more aspects of the patterning process, etc.) one or more parameters of interest, such as the critical dimension (CD) of a structure, the overlay error between successive layers (i.e., the undesired and unintentional misalignment of successive layers) formed in or on the substrate, etc.

It is desirable to determine such one or more parameters of interest for structures created by a patterning process and use them for design, control and/or monitoring relating to the patterning process, e.g., for process design, control and/or verification. The determined one or more parameters of interest of patterned structures can be used for patterning process design, correction and/or verification, defect detection or classification, yield estimation and/or process control.

Thus, in patterning processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Various forms of inspection apparatus (e.g., metrology apparatus) have been developed for use in the lithographic field. These devices direct a beam of radiation onto a target and measure one or more properties of the redirected (e.g., scattered) radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

A further technique is involves having the zeroth order of diffraction (corresponding to a specular reflection) blocked, and only higher orders are processed. Examples of such metrology can be found in PCT patent application publication nos. WO 2009/078708 and WO 2009/106279, which are hereby incorporated by reference in their entirety. Further developments of the technique have been described in U.S. patent application publication nos. US 2011-0027704, US 2011-0043791 and US 2012-0242940, each of which is incorporated herein in its entirety. Such diffraction-based techniques are typically used to measure overlay. The targets for techniques can be smaller than the illumination spot and may be surrounded by product structures on a substrate. A target can comprise multiple periodic structures, which can be measured in one image. In a particular form of such a metrology technique, overlay measurement results are obtained by measuring a target twice under certain conditions, while either rotating the target or changing the illumination mode or imaging mode to obtain separately the $-1^{st}$ and the $+1^{st}$ diffraction order intensities. The intensity asymmetry, a comparison of these diffraction order intensities, for a given target provides a measurement of target asymmetry, that is asymmetry in the target. This asymmetry in the target can be used as an indicator of overlay error.

SUMMARY

In the example of overlay measurement, they rely on an assumption that overlay (i.e., overlay error and deliberate bias) is the only cause of target asymmetry in the target. Any other asymmetry in the target, such as structural asymmetry of features within the periodic structure in an upper layer, within the periodic structure in a lower layer overlaid by the periodic structure in the upper layer, or both, also causes an intensity asymmetry in the $1^{st}$ (or other higher) orders. This intensity asymmetry attributable to such other asymmetry in the target, and which is not related to overlay (including an intentional bias), perturbs the overlay measurement, giving an inaccurate overlay measurement. Asymmetry in the lower or bottom periodic structure of a target is a common form of structural asymmetry. It may originate for example in substrate processing steps such as chemical-mechanical polishing (CMP), performed after the bottom periodic structure was originally formed.

In an embodiment, there is provided a method comprising: evaluating a plurality of substrate measurement recipes for measurement of a metrology target processed using a patterning process, against stack sensitivity and overlay sensitivity; and selecting one or more substrate measurement recipes from the plurality of substrate measurement recipes that have a value of the stack sensitivity that meets or crosses a threshold and that have a value of the overlay sensitivity within a certain finite range from a maximum or minimum value of the overlay sensitivity.

In an embodiment, there is provided a method comprising: evaluating a plurality of substrate measurement recipes for measurement of a metrology target on a substrate processed using a patterning process, against a robustness indicator representing statistical variation of a sensitivity parameter across the substrate; and selecting one or more substrate measurement recipes from the plurality of substrate measurement recipes that have the robustness indicator that meets or crosses a threshold.

In an embodiment, there is provided a method comprising: evaluating a plurality of substrate measurement recipes for measurement of a metrology target on a substrate processed using a patterning process, against a stack difference parameter, the stack difference parameter representing an un-designed difference in physical configuration between adjacent periodic structures of the metrology target or between the metrology target and another adjacent target on the substrate; and selecting one or more substrate measurement recipes from the plurality of substrate measurement recipes that have the stack difference parameter that meets or crosses a threshold.

In an embodiment, there is provided a metrology apparatus for measuring a parameter of a lithographic process, the metrology apparatus being operable to perform a method as described herein.

In an embodiment, there is provided a non-transitory computer program product comprising machine-readable instructions for causing a processor to cause performance of a method as described herein.

In an embodiment, there is provided a system comprising: an inspection apparatus configured to provide a beam of radiation on two adjacent periodic structures or measurement targets on a substrate and to detect radiation diffracted by the targets to determine a parameter of a patterning process; and a non-transitory computer program as described herein. In an embodiment, the system further comprises a lithographic apparatus comprising a support structure configured to hold a patterning device to modulate a radiation beam and a projection optical system arranged to project the modulated radiation beam onto a radiation-sensitive substrate.

Further features and advantages, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments will now be described, by way of example only, with reference to the accompanying drawings in which;

FIG. 4 schematically depicts an example inspection apparatus;

FIG. 5 illustrates the relationship between an illumination spot of an inspection apparatus and a metrology target;

FIG. 7A depicts a schematic diagram of an inspection apparatus (e.g., a dark field scatterometer in this case) configured to measure a target using a first pair of illumination apertures;

FIG. 7B schematically depicts a detail of a diffraction spectrum of a target periodic structure for a given direction of illumination;

FIG. 7C schematically depicts a second pair of illumination apertures providing further illumination modes in using the inspection apparatus of FIG. 7A for diffraction based overlay measurements;

FIG. 7D schematically depicts a third pair of illumination apertures combining the first and second pair of apertures;

FIG. 8 depicts a form of multiple periodic structure target and an outline of a measurement spot on a substrate;

FIG. 9 depicts an image of the target of FIG. 8 obtained in the inspection apparatus of FIG. 7A;

FIG. 11A, FIG. 11B and FIG. 11C respectively show schematic cross-sections of overlay periodic structures having different overlay values in the region of zero;

FIG. 11D is a schematic cross-section of an overlay periodic structure having structural asymmetry in a bottom periodic structure due to processing effects;

DETAILED DESCRIPTION

Before describing embodiments in detail, it is instructive to present an example environment in which embodiments may be implemented.

Figure 1:
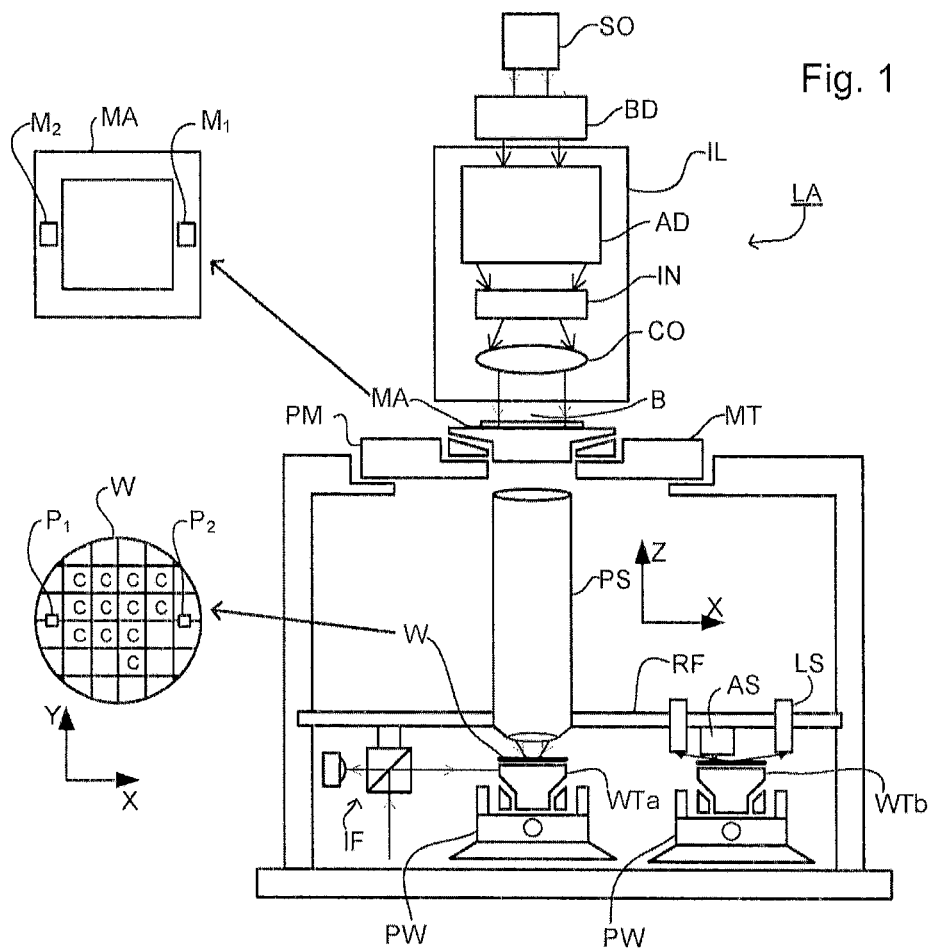
FIG. 1 depicts an embodiment of a lithographic apparatus.

FIG. 1 schematically depicts a lithographic apparatus LA. The apparatus includes an illumination optical system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection optical system (e.g., a refractive projection lens system) PS configured to project a pattern imparted to the radiation beam B by patterning device MA onto a target portion C (e.g., including one or more dies) of the substrate W.

The illumination optical system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table) MT, and is patterned by the patterning device. Having traversed the patterning device (e.g., mask) MA, the radiation beam B passes through the projection optical system PS, which focuses the beam onto a target portion C of the substrate W, thereby projecting an image of the pattern on the target portion C. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using patterning device alignment marks $M_1$, $M_2$ and substrate alignment marks $P_1$, $P_2$. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the patterning device alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

Lithographic apparatus LA in this example is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus.

The depicted apparatus can be used in a variety of modes, including for example a step mode or a scan mode. The construction and operation of lithographic apparatus is well known to those skilled in the art and need not be described further for an understanding of the embodiments of the present invention.

Figure 2:
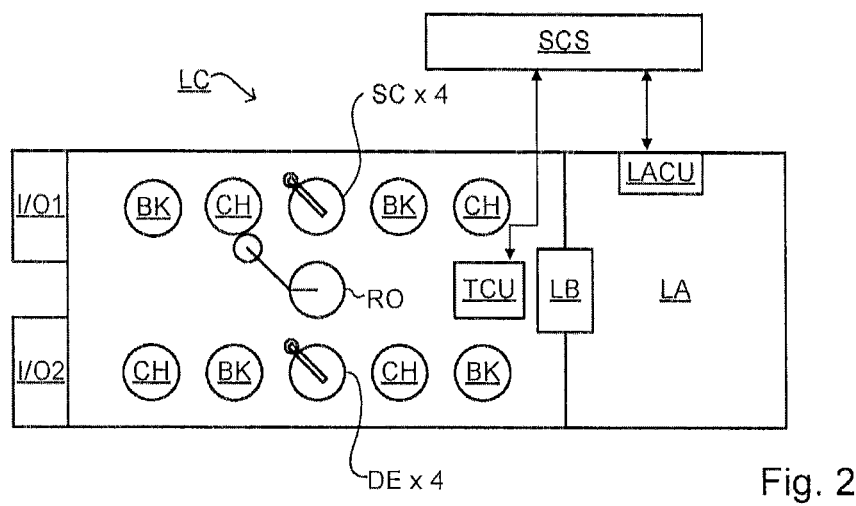
FIG. 2 depicts an embodiment of a lithographic cell or cluster.

As shown in FIG. 2, the lithographic apparatus LA forms part of a lithographic system, referred to as a lithographic cell LC or a lithocell or cluster. The lithographic cell LC may also include apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order to design, monitor, control, etc. the patterning process (e.g., a device manufacturing process) that includes at least one patterning step (e.g., an optical lithography step), the patterned substrate can be inspected and one or more parameters of the patterned substrate are measured. The one or more parameters may include, for example, overlay between successive layers formed in or on the patterned substrate, critical dimension (CD) (e.g., critical linewidth) of, for example, features formed in or on the patterned substrate, focus or focus error of an optical lithography step, dose or dose error of an optical lithography step, optical aberrations of an optical lithography step, etc. This measurement may be performed on a target of the product substrate itself and/or on a dedicated metrology target provided on a substrate. There are various techniques for making measurements of the structures formed in the patterning process, including the use of a scanning electron microscope, image-based measurement or inspection tools and/or various specialized tools. A relatively fast and non-invasive form of specialized metrology and/or inspection tool is one in which a beam of radiation is directed onto a target on the surface of the substrate and properties of the scattered (diffracted/reflected) beam are measured. By comparing one or more properties of the beam before and after it has been scattered by the substrate, one or more properties of the substrate can be determined. This may be termed diffraction-based metrology or inspection.

Figure 3:
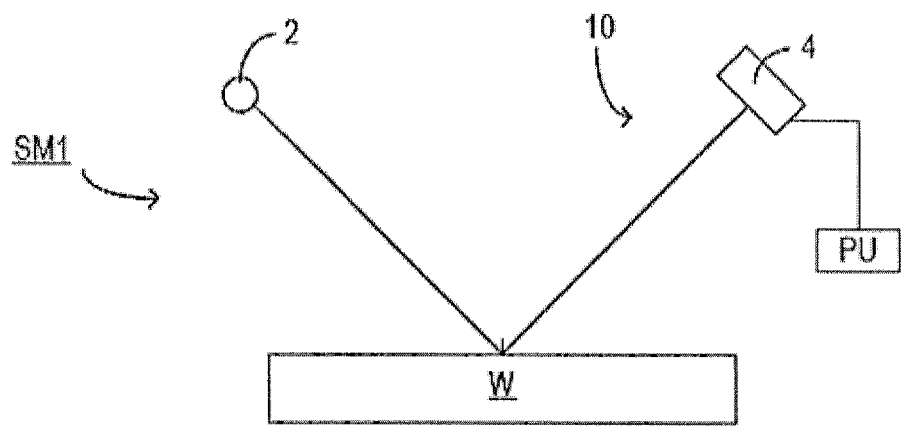
FIG. 3 schematically depicts an example inspection apparatus and metrology technique.
Figure 3:
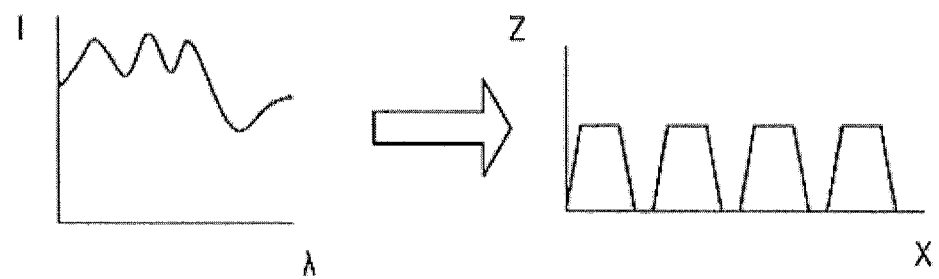

FIG. 3 depicts an example inspection apparatus (e.g., a scatterometer). It comprises a broadband (white light) radiation projector 2 which projects radiation onto a substrate W. The redirected radiation is passed to a spectrometer detector 4, which measures a spectrum 10 (intensity as a function of wavelength) of the specular reflected radiation, as shown, e.g., in the graph in the lower left. From this data, the structure or profile giving rise to the detected spectrum may be reconstructed by processor PU, e.g. by Rigorous Coupled Wave Analysis and non-linear regression or by comparison with a library of simulated spectra as shown at the bottom right of FIG. 3. In general, for the reconstruction the general form of the structure is known and some variables are assumed from knowledge of the process by which the structure was made, leaving only a few variables of the structure to be determined from the measured data. Such an inspection apparatus may be configured as a normal-incidence inspection apparatus or an oblique-incidence inspection apparatus.

Another inspection apparatus that may be used is shown in FIG. 4. In this device, the radiation emitted by radiation source 2 is collimated using lens system 120 and transmitted through interference filter 130 and polarizer 170, reflected by partially reflecting surface 160 and is focused into a spot S on substrate W via an objective lens 150, which has a high numerical aperture (NA), desirably at least 0.9 or at least 0.95. An immersion inspection apparatus (using a relatively high refractive index fluid such as water) may even have a numerical aperture over 1.

As in the lithographic apparatus LA, one or more substrate tables may be provided to hold the substrate W during measurement operations. The substrate tables may be similar or identical in form to the substrate table WT of FIG. 1. In an example where the inspection apparatus is integrated with the lithographic apparatus, they may even be the same substrate table. Coarse and fine positioners may be provided to a second positioner PW configured to accurately position the substrate in relation to a measurement optical system. Various sensors and actuators are provided for example to acquire the position of a target of interest, and to bring it into position under the objective lens 150. Typically many measurements will be made on targets at different locations across the substrate W. The substrate support can be moved in X and Y directions to acquire different targets, and in the Z direction to obtain a desired location of the target relative to the focus of the optical system. It is convenient to think and describe operations as if the objective lens is being brought to different locations relative to the substrate, when, for example, in practice the optical system may remain substantially stationary (typically in the X and Y directions, but perhaps also in the Z direction) and only the substrate moves. Provided the relative position of the substrate and the optical system is correct, it does not matter in principle which one of those is moving in the real world, or if both are moving, or a combination of a part of the optical system is moving (e.g., in the Z and/or tilt direction) with the remainder of the optical system being stationary and the substrate is moving (e.g., in the X and Y directions, but also optionally in the Z and/or tilt direction).

The radiation redirected by the substrate W then passes through partially reflecting surface 160 into a detector 180 in order to have the spectrum detected. The detector 180 may be located at a back-projected focal plane 110 (i.e., at the focal length of the lens system 150) or the plane 110 may be re-imaged with auxiliary optics (not shown) onto the detector 180. The detector may be a two-dimensional detector so that a two-dimensional angular scatter spectrum of a substrate target 30 can be measured. The detector 180 may be, for example, an array of CCD or CMOS sensors, and may use an integration time of, for example, 40 milliseconds per frame.

A reference beam may be used, for example, to measure the intensity of the incident radiation. To do this, when the radiation beam is incident on the partially reflecting surface 160 part of it is transmitted through the partially reflecting surface 160 as a reference beam towards a reference mirror 140. The reference beam is then projected onto a different part of the same detector 180 or alternatively on to a different detector (not shown).

One or more interference filters 130 are available to select a wavelength of interest in the range of, say, 405-790 nm or even lower, such as 200-300 nm. The interference filter may be tunable rather than comprising a set of different filters. A grating could be used instead of an interference filter. An aperture stop or spatial light modulator (not shown) may be provided in the illumination path to control the range of angle of incidence of radiation on the target.

The detector 180 may measure the intensity of redirected radiation at a single wavelength (or narrow wavelength range), the intensity separately at multiple wavelengths or integrated over a wavelength range. Furthermore, the detector may separately measure the intensity of transverse magnetic- and transverse electric-polarized radiation and/or the phase difference between the transverse magnetic- and transverse electric-polarized radiation.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may be etched into or on the substrate (e.g., into one or more layers on the substrate). The pattern (e.g., of bars, pillars or vias) is sensitive to change in processing in the patterning process (e.g., optical aberration in the lithographic projection apparatus (particularly the projection system PS), focus change, dose change, etc.) and will manifest in a variation in the printed grating. Accordingly, the measured data of the printed grating is used to reconstruct the grating. One or more parameters of the 1-D grating, such as line width and/or shape, or one or more parameters of the 2-D grating, such as pillar or via width or length or shape, may be input to the reconstruction process, performed by processor PU, from knowledge of the printing step and/or other inspection processes.

In addition to measurement of a parameter by reconstruction, diffraction-based metrology or inspection can be used in the measurement of asymmetry of features in product and/or resist patterns. A particular application of asymmetry measurement is for the measurement of overlay, for example, but other applications are also known. In this case, the target 30 typically comprises one set of periodic features superimposed on another. For example, asymmetry can be measured by comparing opposite parts of the diffraction spectrum from the target 30 (for example, comparing the −1st and +1$^{st}$ orders in the diffraction spectrum of a periodic grating). The concepts of asymmetry measurement using the instrument of FIG. 3 or FIG. 4 are described, for example, in U.S. patent application publication US20060066855, which is incorporated herein in its entirety by reference. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 4, where detector 180 may be an image sensor, such asymmetry in the diffraction orders appears directly as asymmetry in the pupil image recorded by detector 180. This asymmetry can be measured by digital image processing in unit PU, and calibrated against known values of overlay.

FIG. 5 illustrates a plan view of a typical target 30, and the extent of illumination spot S in the apparatus of FIG. 4. To obtain a diffraction spectrum that is free of interference from surrounding structures, the target 30, in an embodiment, is a periodic structure (e.g., grating) larger than the width (e.g., diameter) of the illumination spot S. The width of spot S may be smaller than the width and length of the target. The target in other words is 'underfilled' by the illumination, and the diffraction signal is essentially free from any signals from product features and the like outside the target itself. The illumination arrangement 2, 120, 130, 170 may be configured to provide illumination of a uniform intensity across a back focal plane of objective 150. Alternatively, by, e.g., including an aperture in the illumination path, illumination may be restricted to on axis or off axis directions.

Figure 6:
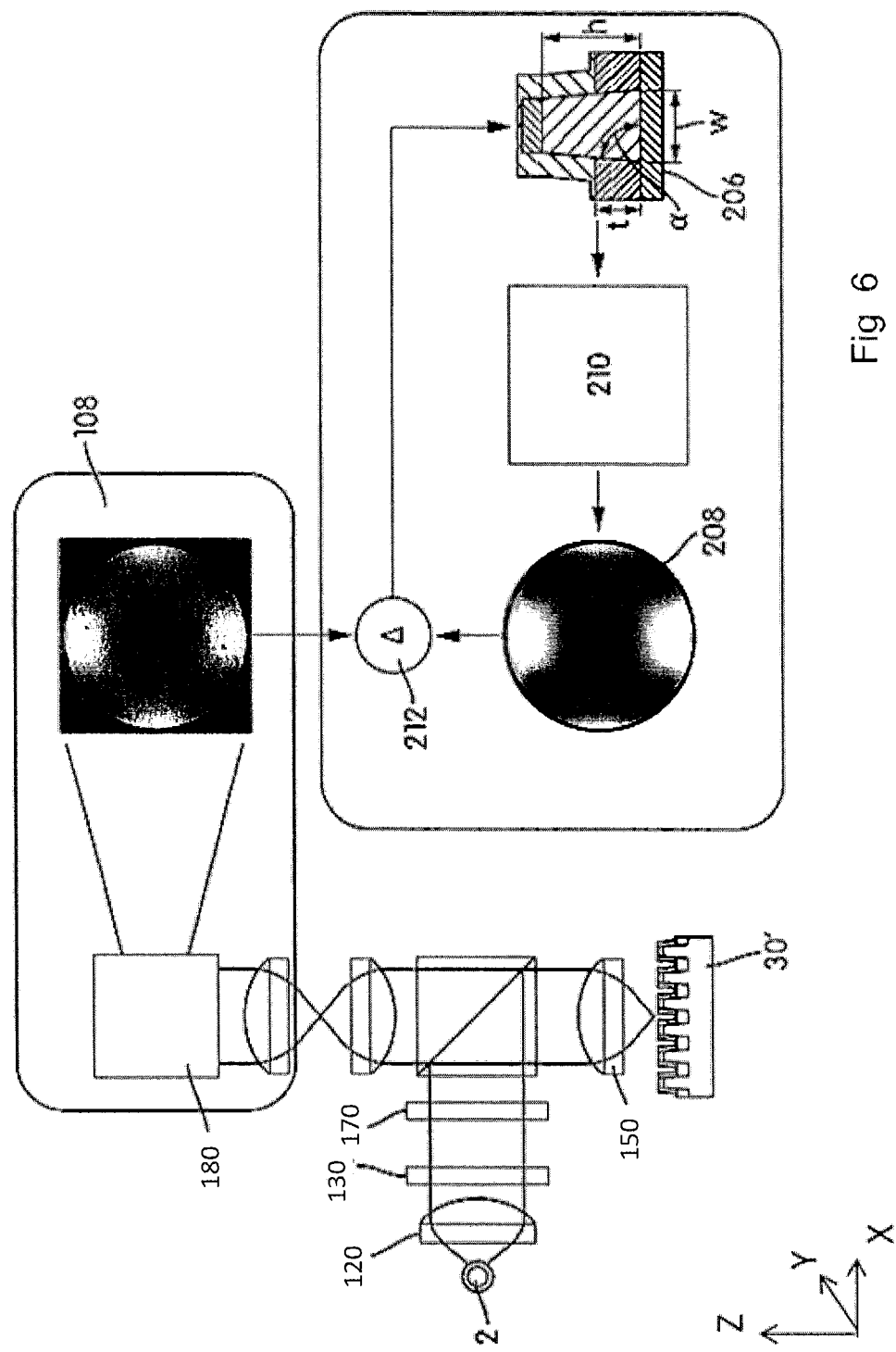
FIG. 6 schematically depicts a process of deriving a plurality of variables of interest based on measurement data.

FIG. 6 schematically depicts an example process of the determination of the value of one or more variables of interest of a target pattern 30' based on measurement data obtained using metrology. Radiation detected by the detector 180 provides a measured radiation distribution 108 for target 30'.

For a given target 30', a radiation distribution 208 can be computed/simulated from a parameterized model 206 using, for example, a numerical Maxwell solver 210. The parameterized model 206 shows example layers of various materials making up, and associated with, the target. The parameterized model 206 may include one or more of variables for the features and layers of the portion of the target under consideration, which may be varied and derived. As shown in FIG. 6, the one or more of the variables may include the thickness t of one or more layers, a width w (e.g., CD) of one or more features, a height h of one or more features, and/or a sidewall angle α of one or more features. Although not shown, the one or more of the variables may further include, but is not limited to, the refractive index (e.g., a real or complex refractive index, refractive index tensor, etc.) of one or more of the layers, the extinction coefficient of one or more layers, the absorption of one or more layers, resist loss during development, a footing of one or more features, and/or line edge roughness of one or more features. The initial values of the variables may be those expected for the target being measured. The measured radiation distribution 108 is then compared at 212 to the computed radiation distribution 208 to determine the difference between the two. If there is a difference, the values of one or more of the variables of the parameterized model 206 may be varied, a new computed radiation distribution 208 calculated and compared against the measured radiation distribution 108 until there is sufficient match between the measured radiation distribution 108 and the computed radiation distribution 208. At that point, the values of the variables of the parameterized model 206 provide a good or best match of the geometry of the actual target 30'. In an embodiment, there is sufficient match when a difference between the measured radiation distribution 108 and the computed radiation distribution 208 is within a tolerance threshold.

A further inspection apparatus suitable for use in embodiments is shown in FIG. 7A. A target T and diffracted rays of measurement radiation used to illuminate the target are illustrated in more detail in FIG. 7B. The inspection apparatus illustrated is of a type known as a dark field metrology apparatus. The inspection apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by source 11 (e.g., a xenon lamp) is directed onto substrate W via optical element 15 by an optical system comprising lenses 12, 14 and objective lens 16. These lenses are arranged in a double sequence of a 4F arrangement. A different lens arrangement can be used, provided that it, e.g., provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis radiation from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary radiation outside the desired illumination mode will interfere with the desired measurement signals.

As shown in FIG. 7B, target T is placed with substrate W normal to the optical axis O of objective lens 16. The substrate W may be supported by a support (not shown). A ray of measurement radiation I impinging on target T from an angle off the axis O gives rise to a zeroth order ray (solid line O) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitches of the targets and the illumination angles can be designed or adjusted so that the first order rays entering the objective lens are closely aligned with the central optical axis. The rays illustrated in FIGS. 7A and 7B are shown somewhat off axis, purely to enable them to be more easily distinguished in the diagram.

At least the 0 and +$1^{st}$ orders diffracted by the target T on substrate W are collected by objective lens 16 and directed back through optical element 15. Returning to FIG. 7A, both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the inspection apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the periodic structure features as such will not be formed, if only one of the $-1^{st}$ and $+1^{st}$ orders is present.

The particular forms of aperture plate 13 and field stop 21 shown in FIGS. 7A, 7C and 7D are purely examples. In an embodiment, on-axis illumination of the targets is used and an aperture stop with an off-axis aperture is used to pass substantially only one first order of diffracted radiation to the sensor. In yet other embodiments, 2nd, 3rd and higher order beams (not shown in FIG. 7A, 7B, 7C or 7D) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure periodic structures oriented in one direction (X or Y depending on the set-up). For measurement of an orthogonal periodic structure, rotation of the target through 90° and 270° might be implemented. Different aperture plates are shown in FIGS. 7C and 7D. The use of these, and numerous other variations and applications of the apparatus are described in the patent application publications mentioned above.

FIG. 8 depicts a (composite) target formed on a substrate according to known practice. The target in this example comprises four periodic structures (e.g., gratings) 32 to 35 positioned closely together so that they will all be within a measurement spot 31 formed by the metrology radiation illumination beam of the inspection apparatus. The four periodic structures thus are all simultaneously illuminated and simultaneously imaged on sensors 19 and 23. In an example dedicated to measurement of overlay, periodic structures 32 to 35 are themselves composite periodic structures formed by overlying periodic structures that are patterned in different layers of, e.g., the semiconductor device formed on substrate W. Periodic structures 32 to 35 may have differently biased overlay offsets in order to facilitate measurement of overlay between the layers in which the different parts of the composite periodic structures are formed. The meaning of overlay bias will be explained below with reference to FIG. 8. Periodic structures 32 to 35 may also differ in their orientation, as shown, so as to diffract incoming radiation in X and Y directions. In one example, periodic structures 32 and 34 are X-direction periodic structures with bias offsets of +d, −d, respectively. Periodic structures 33 and 35 are Y-direction periodic structures with bias offsets +d, −d respectively. Separate images of these periodic structures can be identified in the image captured by sensor 23. This is only one example of a target. A target may comprise more or fewer than 4 periodic structures, or only a single periodic structure.

FIG. 9 shows an example of an image that may be formed on and detected by the sensor 23, using the target of FIG. 8 in the apparatus of FIG. 7, using the aperture plates 13NW or 13SE from FIG. 7D. While the pupil plane image sensor 19 cannot resolve the different individual periodic structures 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small target periodic structures 32 to 35. If the targets are located in product areas, product features may also be visible in the periphery of this image field. Image processor and control system PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the patterning process. Overlay performance is an important example of such a parameter.

Figure 10:
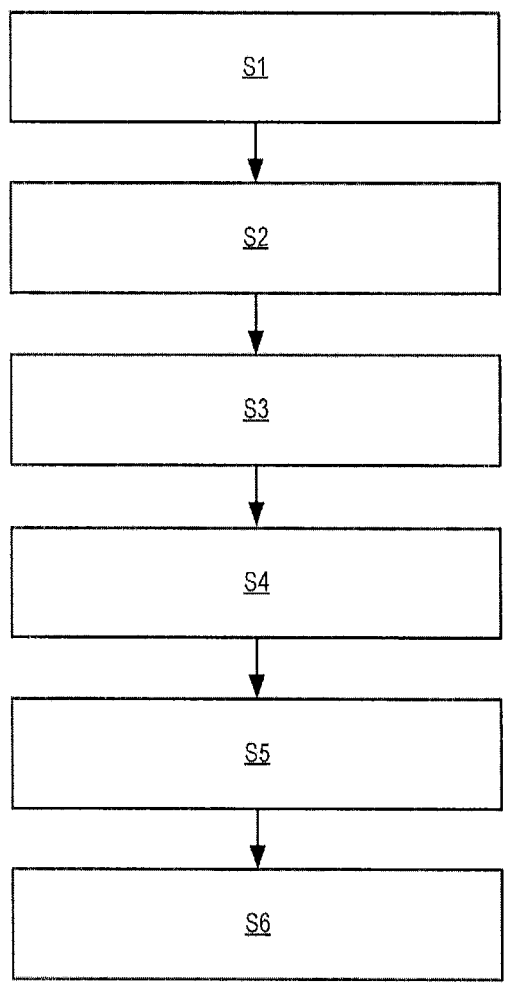
FIG. 10 is a flowchart showing steps of an overlay measurement method using the inspection apparatus of FIG. 3.

FIG. 10 illustrates how, using for example the method described in PCT patent application publication no. WO 2011/012624 (incorporated herein in its entirety by reference), overlay error (i.e., undesired and unintentional overlay misalignment) between the two layers containing the component periodic structures 32 to 35 is measured. This measurement is done through identifying target asymmetry, as revealed by comparing the intensities in the $+1^{st}$ order and $-1^{st}$ order images of the target periodic structures (the intensities of other corresponding higher orders can be compared, e.g. $+2^{nd}$ and $-2^{nd}$ orders) to obtain a measure of the intensity asymmetry. At step S1, the substrate, for example a semiconductor wafer, is processed through a lithographic apparatus, such as the lithographic cell of FIG. 2, one or more times, to create a target including the periodic structures 32-35. At S2, using the inspection apparatus of FIG. 7, an image of the periodic structures 32 to 35 is obtained using only one of the first order diffracted beams (say −1). At step S3, whether by changing the illumination mode, or changing the imaging mode, or by rotating substrate W by 180° in the field of view of the inspection apparatus, a second image of the periodic structures using the other first order diffracted beam (+1) can be obtained. Consequently the +1 diffracted radiation is captured in the second image.

Note that, by including only half of the first order diffracted radiation in each image, the 'images' referred to here are not conventional dark field microscopy images. The individual target features of the target periodic structures will not be resolved. Each target periodic structure will be represented simply by an area of a certain intensity level. In step S4, a region of interest (ROI) is identified within the image of each component target periodic structure, from which intensity levels will be measured.

Having identified the ROI for each individual target periodic structure and measured its intensity, the asymmetry of the target, and hence overlay error, can then be determined. This is done (e.g., by the processor PU) in step S5 comparing the intensity values obtained for $+1^{st}$ and $-1^{st}$ orders for each target periodic structure 32-35 to identify their intensity asymmetry, e.g., any difference in their intensity. The term "difference" is not intended to refer only to subtraction. Differences may be calculated in ratio form. In step S6 the measured intensity asymmetries for a number of target periodic structures are used, together with knowledge of any known imposed overlay biases of those target periodic structures, to calculate one or more performance parameters of the patterning process in the vicinity of the target T.

FIGS. 11A-11D show schematic cross sections of target periodic structures (overlay periodic structures), with different bias offsets. These can be used as the target T on substrate W, as seen in FIGS. 7-9. Periodic structures with periodicity in the X direction are shown for the sake of example only. Different combinations of these periodic structures with different biases and with different orientations can be provided separately or as part of a target.

Starting with FIG. 11A, a target 600 formed in at least two layers, labeled L1 and L2, is shown. In the lower or bottom layer L1, a first periodic structure (the lower or bottom periodic structure), for example a grating, is formed by features 602 and spaces 604 on a substrate 606. In layer L2, a second periodic structure, for example a grating, is formed by features 608 and spaces 610. (The cross-section is drawn such that the features 602, 608 (e.g., lines) extend into the page.) The periodic structure pattern repeats with a pitch P in both layers. Features 602 and 608 may take the form of lines, dots, blocks and via holes. In the situation shown at FIG. 11A, there is no overlay contribution due to misalignment, e.g., no overlay error and no imposed bias, so that each feature 608 of the second structure lies exactly over a feature 602 in the first structure.

At FIG. 11B, the same target with a first known imposed bias +d is shown, such that the features 608 of the first structure are shifted by a distance d to the right, relative to the features of the second structure. The bias distance d might be a few nanometers in practice, for example 10 nm-20 nm, while the pitch P is for example in the range 300-1000 nm, for example 500 nm or 600 nm. At FIG. 11C, another feature with a second known imposed bias −d, such that the features of 608 are shifted to the left, is depicted. The value of d need not be the same for each structure. Biased periodic structures of this type shown at FIGS. 11A to 11C are described in the prior patent application publications mentioned above.

FIG. 11D shows schematically a phenomenon of structural asymmetry, in this case structural asymmetry in the first structure (bottom structure asymmetry). The features in the periodic structures at FIGS. 11A to 11C, are shown as perfectly square-sided, when a real feature would have some slope on the side, and a certain roughness. Nevertheless they are intended to be at least symmetrical in profile. The features 602 and/or spaces 604 at FIG. 11D in the first structure no longer have a symmetrical form at all, but rather have become distorted by one or more processing steps. Thus, for example, a bottom surface of each space has become tilted (bottom wall tilt). For example, side wall angles of the features and spaces have become asymmetrical. As a result of this, the overall target asymmetry of a target will comprise an overlay contribution independent of structural asymmetry (i.e., an overlay contribution due to misalignment of the first structure and second structure;

itself comprised of overlay error and any known imposed bias) and a structural contribution due to this structural asymmetry in the target.

When overlay is measured by the method of FIG. 10 using only two biased periodic structures, the process-induced structural asymmetry cannot be distinguished from the overlay contribution due to misalignment, and overlay measurements (in particular to measure the undesired overlay error) become unreliable as a result. Structural asymmetry in the first structure (bottom periodic structure) of a target is a common form of structural asymmetry. It may originate, for example, in the substrate processing steps such as chemical-mechanical polishing (CMP), performed after the first structure was originally formed.

In PCT patent application publication no. WO 2013-143814, it is proposed to use three or more component periodic structures to measure overlay by a modified version of the method of FIG. 10. Three or more periodic structures of the type shown in FIGS. 11A to 11C are used to obtain overlay measurements that are to some extent corrected for structural asymmetry in the target periodic structures, such as is caused by bottom structure asymmetry in a practical patterning process. However, this method requires a new target design (e.g. different to that illustrated in FIG. 8) and therefore a new patterning device or patterning device pattern will be required. Furthermore, the target area is larger and therefore consumes more substrate area. In addition, the phase element of the overlay contribution resultant from structural asymmetry is ignored in this and other prior methods, meaning that the corrections are not as accurate as they could be if the phase element was also corrected for.

Figure 12:
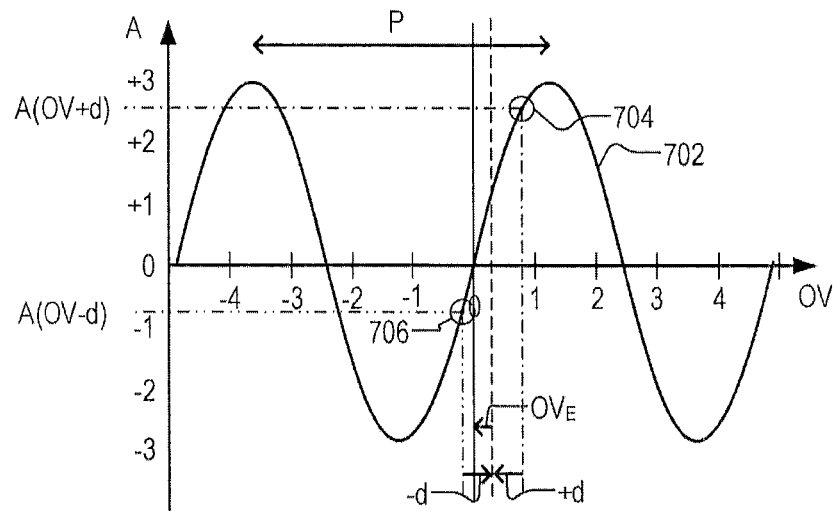
FIG. 12 illustrates principles of overlay measurement in an ideal target, not subject to structural asymmetry.
Figure 13:
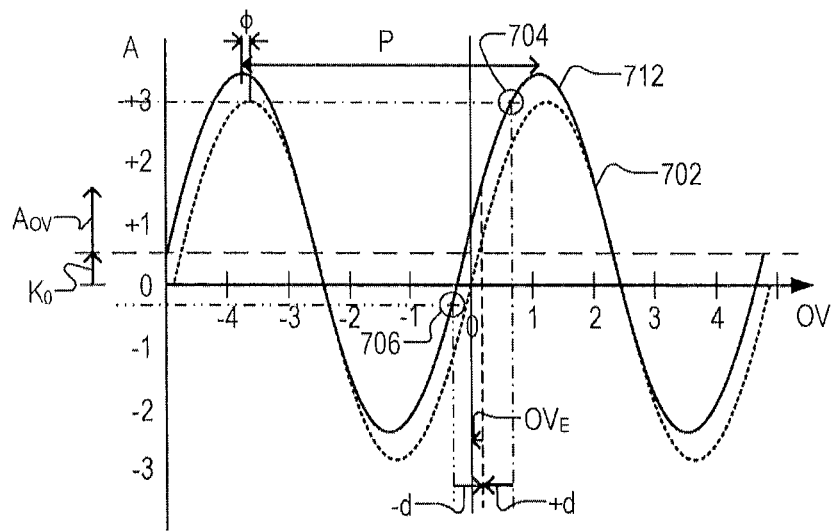
FIG. 13 illustrates principles of overlay measurement in a non-ideal target, with correction of structural asymmetry as disclosed in embodiments herein.

In FIG. 12 a curve 702 illustrates the relationship between overlay OV and intensity asymmetry A for an 'ideal' target having zero offset and no structural asymmetry within the individual periodic structures forming the target, and in particular within the individual periodic structure of the first structure. Consequently, the target asymmetry of this ideal target comprises only an overlay contribution due to misalignment of the first structure and second structure resultant from a known imposed bias and overlay error $OV_E$. This graph, and the graph of FIG. 13, illustrate the principles behind the disclosure only, and in each graph, the units of intensity asymmetry A and overlay OV are arbitrary. Examples of actual dimensions will be given further below.

In the 'ideal' situation of FIG. 12, the curve 702 indicates that the intensity asymmetry A has a non-linear periodic relationship (e.g., sinusoidal relationship) with the overlay. The period P of the sinusoidal variation corresponds to the period or pitch P of the periodic structures, converted of course to an appropriate scale. The sinusoidal form is pure in this example, but can include harmonics in real circumstances.

As mentioned above, biased periodic structures (having a known imposed overlay bias) can be used to measure overlay, rather than relying on a single measurement. This bias has a known value defined in the patterning device (e.g. a reticle) from which it was made, that serves as an on-substrate calibration of the overlay corresponding to the measured intensity asymmetry. In the drawing, the calculation is illustrated graphically. In steps S1-S5, intensity asymmetry measurements $A_{+d}$ and $A_{-d}$ are obtained for periodic structures having imposed biases +d and −d respectively (as shown in FIG. 11B and FIG. 11C, for example). Fitting these measurements to the sinusoidal curve gives points 704 and 706 as shown. Knowing the biases, the true overlay error $OV_E$ can be calculated. The pitch P of the sinusoidal curve is known from the design of the target. The vertical scale of the curve 702 is not known to start with, but is an unknown factor which can be referred to as a 1st harmonic proportionality constant, K. Thus, overlay sensitivity K is a measure of the sensitivity of the intensity asymmetry measurements to overlay. In an embodiment, it is a proportionality of the measured intensity with respect to overlay. It thus helps detect process dependency of overlay.

In equation terms, the relationship between overlay error $OV_E$ and intensity asymmetry A is assumed to be:

$$A_{\pm d}=K \sin(OV_E \pm d) \tag{1}$$

where overlay error $OV_E$ is expressed on a scale such that the target pitch P corresponds to an angle $2\pi$ radians. Using two measurements of gratings with different, known biases (e.g. +d and −d), the overlay error $OV_E$ can be calculated using:

$$OV_E = \operatorname{atan}\left(\frac{A_{+d} + A_{-d}}{A_{+d} - A_{-d}} \cdot \tan(d)\right) \tag{2}$$

FIG. 13 shows a first effect of introducing structural asymmetry, for example the bottom periodic structure asymmetry illustrated in FIG. 11D. The 'ideal' sinusoidal curve 702 no longer applies. However, at least approximately, bottom periodic structure asymmetry or other structural asymmetry has the effect of adding an intensity shift term $K_0$ and a phase shift term $\phi$ to the intensity asymmetry $A_{\pm d}$. The resulting curve is shown as 712 in the diagram, with label $K_0$ indicating the intensity shift term, and label $\phi$ indicating the phase offset term. The intensity shift term $K_0$ and phase shift term $\phi$ are dependent upon a combination of the target and a selected characteristic of the measurement radiation, such as the wavelength and/or polarization of the measurement radiation, and is sensitive to process variations. In equation terms, the relationship used for calculation in step S6 becomes:

$$A_{\pm d}=K_0 K \sin(OV_E \pm d+\phi) \tag{3}$$

Where there is structural asymmetry, the overlay model described by equation (2) will provide overlay error values which are impacted by the intensity shift term $K_0$ and phase shift term $\phi$, and will be inaccurate as a consequence. The structural asymmetry will also result in differences in measurements of the same target using one or more different measurement parameters (e.g., wavelength of the measurement beam, polarization of the measurement beam, etc.), when mapping the overlay error, because intensity and phase shift are, e.g., wavelength and/or polarization dependent.

The overlay calculations of modified step S6 rely on certain assumptions. Firstly, it is assumed intensity asymmetry behaves as a sine function of the overlay, with the period P corresponding to the grating pitch. These assumptions are valid for present overlay ranges. The number of harmonics can be designed to be small, because the small pitch-wavelength ratio only allows for a small number of propagating diffraction orders from the grating. However, in practice the overlay contribution to the intensity asymmetry due to misalignment may not necessarily be truly sinusoidal, and may not necessarily be completely symmetrical about OV=0.

So, the effect of structural asymmetry can be generally formulated as:

$$\Delta I_+ = K(OV+d)+\Delta I_{BG} \tag{4}$$

$$\Delta I_- = K(OV-d)+\Delta I_{BG} \tag{5}$$

where $\Delta I_-$ (also synonymous with $A_-$) and $\Delta I_+$ (also synonymous with $A_+$) represent the intensity asymmetry measured and $\Delta I_{BP}$ is the contribution to the intensity asymmetry of the structural asymmetry. And so, the overlay error $\Delta OV$ can be considered as a function of $\Delta I_{BP}/K$.

Now, it has been further discovered that, in addition to or alternatively to structural asymmetry in a target, a stack difference between adjacent periodic structures of a target or between adjacent targets may be a factor that adversely affects the accuracy of measurement, such as overlay measurement. Stack difference may be understood as an un-designed difference in physical configurations between adjacent periodic structures or targets. Stack difference causes a difference in an optical property (e.g., intensity, polarization, etc.) of measurement radiation between the adjacent periodic structures or targets that is due to other than overlay error, other than intentional bias and other than structural asymmetry common to the adjacent periodic structures or targets. Stack difference includes, but is not limited to, a thickness difference between the adjacent periodic structures or targets (e.g., a difference in thickness of one or more layers such that one periodic structure or target is higher or lower than another periodic structure or target designed to be at a substantially equal level), a refractive index difference between the adjacent periodic structures or targets (e.g., a difference in refractive index of one or more layers such that the combined refractive index for the one or more layers for one periodic structure or target is different than the combined refractive index for the one or more layers for of another periodic structure or target even though designed to have a substantially equal combined refractive index), a difference in material between the adjacent periodic structures or targets (e.g., a difference in the material type, material uniformity, etc. of one or more layers such that there is a difference in material for one periodic structure or target from another periodic structure or target designed to have a substantially same material), a difference in the grating period of the structures of adjacent periodic structures or targets (e.g., a difference in the grating period for one periodic structure or target from another periodic structure or target designed to have a substantially same grating period), a difference in depth of the structures of adjacent periodic structures or targets (e.g., a difference due to etching in the depth of structures of one periodic structure or target from another periodic structure or target designed to have a substantially same depth), a difference in width (CD) of the features of adjacent periodic structures or targets (e.g., a difference in the width of features of one periodic structure or target from another periodic structure or target designed to have a substantially same width of features), etc. In some examples, the stack difference is introduced by processing steps, such as CMP, layer deposition, etching, etc. in the patterning process. In an embodiment, periodic structures or targets are adjacent if within 200 µm of each other, within 150 µm of each other, within 100 µm of each other, within 75 µm of each other, within 50 µm of each other, within 40 µm of each other, within 30 µm of each other, within 20 µm of each other, or within 10 µm of each other.

The effect of stack difference (which can be referred to as grating imbalance between gratings) can be generally formulated as:

$$\Delta I_+ = (K+\Delta K)(OV+d) \quad (6)$$

$$\Delta I_- = (K-\Delta K)(OV-d) \quad (7)$$

wherein $\Delta K$ represents a difference in the overlay sensitivity attributable to the stack difference. And so, the overlay error $\Delta OV$ can be proportional to $$\frac{\Delta K}{K}d.$$

So, in order to characterize the stack difference, one or more stack difference parameters can be defined. As noted above, a stack difference parameter is a measure of the un-designed different physical configuration of the adjacent periodic structures or targets. In an embodiment, the stack difference parameter can be determined from evaluating cross-sections of the adjacent periodic structures or targets.

In an embodiment, the stack difference parameter can be determined for lower adjacent gratings of a composite grating by evaluating the lower adjacent gratings before the upper gratings are applied. In an embodiment, the stack difference parameter can be derived from a reconstruction of the adjacent periodic structures or targets from optical measurements of the adjacent periodic structures or targets or from cross-sections of the adjacent periodic structures or targets. That is, the physical dimensions, characteristics, materials properties, etc. are reconstructed and the differences between the adjacent periodic structures or targets are determined to arrive at a stack difference parameter.

An embodiment of the stack difference parameter is a periodic structure intensity imbalance (GI) which can be defined as:

$$GI = 2 * \frac{\hat{I}^{+d} - \hat{I}^{-d}}{\hat{I}^{+d} + \hat{I}^{-d}} \quad (8)$$

where $\hat{I}^{+d}$ is the average of the $+1^{st}$ diffraction order intensity signal diffracted by a first periodic structure having a $+d$ bias, $I_{+1}^{+d}$, and $-1^{st}$ diffraction order intensity signal diffracted by the first periodic structure having the $+d$ bias, $I_{-1}^{+d}$. Similarly, $\hat{I}^{-d}$ is the average of the $+1^{st}$ diffraction order intensity signal diffracted by a second periodic structure having a $-d$ bias, $I_{+1}^{-d}$, and $-1^{st}$ diffraction order intensity signal diffracted by the second periodic structure having the $-d$ bias, $I_{-1}^{-d}$. In an embodiment, the periodic structure intensity imbalance (GI) can be a derived version, such as $$\frac{\hat{I}^{+d} - \hat{I}^{-d}}{\hat{I}^{+d} + \hat{I}^{-d}}, \frac{\hat{I}^{+d} + \hat{I}^{-d}}{\hat{I}^{+d} - \hat{I}^{-d}},$$

etc.

Now, in the face of structural asymmetry, stack difference and any other process variabilities, it would be desirable to derive a combination of target layout, measurement beam wavelength, measurement beam polarization, etc. that would yield an accurate measurement of the desired process parameter (e.g., overlay) and/or that yields measurement values of the desired process parameter that is robust to process variability. Thus, it would be desirable, for example, to arrive at a desirably optimum selection of the target-measurement parameter combination so as to obtain more accurate process parameter measurement and/or that yields measurement values of the desired process parameter that is robust to process variability.

The measurement accuracy and/or sensitivity of the target may vary with respect to one or more attributes of the target itself and/or one or more attributes of the measurement radiation provided onto the target, for example, the wavelength of the radiation, the polarization of the radiation, and/or the intensity distribution (i.e., angular or spatial intensity distribution) of the radiation. In an embodiment, the wavelength range of the radiation is limited to one or more wavelengths selected from a range (e.g., selected from the range of about 400 nm to 900 nm). Further, a selection of different polarizations of the radiation beam may be provided and various illumination shapes can be provided using, for example, a plurality of different apertures.

So, to enable such selection and measurement, a substrate measurement recipe can be used that specifies one or more parameters of the measurement using the measurement system. In an embodiment, the term "substrate measurement recipe" includes one or more parameters of the measurement itself, one or more parameters of a pattern measured, or both.

In this context, a pattern measured (also referred to as a "target" or "target structure") may be a pattern that is optically measured, e.g., whose diffraction is measured. The pattern measured may be a pattern specially designed or selected for measurement purposes. Multiple copies of a target may be placed on many places on a substrate. For example, a substrate measurement recipe may be used to measure overlay. In an embodiment, a substrate measurement recipe may be used to measure another process parameter (e.g., dose, focus, CD, etc.) In an embodiment, a substrate measurement recipe may be used for measuring alignment of a layer of a pattern being imaged against an existing pattern on a substrate; for example, a substrate measurement recipe may be used to align the patterning device to the substrate, by measuring a relative position of the substrate.

In an embodiment, if the substrate measurement recipe comprises one or more parameters of the measurement itself, the one or more parameters of the measurement itself can include one or more parameters relating to a measurement beam and/or measurement apparatus used to make the measurement. For example, if the measurement used in a substrate measurement recipe is a diffraction-based optical measurement, one or more parameters of the measurement itself may include a wavelength of measurement radiation, and/or a polarization of measurement radiation, and/or measurement radiation intensity distribution, and/or an illumination angle (e.g., incident angle, azimuth angle, etc.) relative to the substrate of measurement radiation, and/or the relative orientation relative to a pattern on the substrate of diffracted measurement radiation, and/or number of measured points or instances of the target, and/or the locations of instances of the target measured on the substrate. The one or more parameters of the measurement itself may include one or more parameters of the metrology apparatus used in the measurement, which can include detector sensitivity, numerical aperture, etc.

In an embodiment, if the substrate measurement recipe comprises one or more parameters of a pattern measured, the one or more parameters of the pattern measured may include one or more geometric characteristics (such as a shape of at least part of the pattern, and/or orientation of at least part of the pattern, and/or a pitch of at least part of the pattern (e.g., pitch of a periodic structure including the pitch of an upper periodic structure in a layer above that of a lower periodic structure and/or the pitch of the lower periodic structure), and/or a size (e.g., CD) of at least part of the pattern (e.g., the CD of a feature of a periodic structure, including that of a feature of the upper periodic structure and/or the lower periodic structure), and/or a segmentation of a feature of the pattern (e.g., a division of a feature of a periodic structure into sub-structures), and/or a length of a periodic structure or of a feature of the periodic structure), and/or a materials property (e.g., refractive index, extinction coefficient, material type, etc.) of at least part of the pattern, and/or an identification of the pattern (e.g., distinguishing a pattern being from another pattern), etc.

A substrate measurement recipe may be expressed in a form like $(r_1, r_2, r_3, \ldots r_n; t_1, t_2, t_3, \ldots t_m)$, where $r_i$ are one or more parameters of the measurement and $t_j$ are one or more parameters of one or more patterns measured. As will be appreciated, n and m can be 1. Further, the substrate measurement recipe does not need to have both one or more parameters of the measurement and one or more parameters of one or more patterns measured; it can have just one or more parameters of the measurement or have just one or more parameters of one or more patterns measured.

A target may be subjected to measurement using two substrate measurement recipes A and B, e.g., differ on the stage at which a target is measured (e.g., A measures a target when it comprises a latent image structure and B measures a target when it doesn't comprise a latent image structure) and/or differ on the parameters of their measurement. Substrate measurement recipes A and B can at least differ on the target measured (e.g., A measures a first target and B measures a second different target). Substrate measurement recipes A and B may differ on the parameters of their measurement and target measurement. Substrate measurement recipes A and B may not even be based on the same measurement technique. For example recipe A may be based on diffraction-based measurement and recipe B may be based on scanning electron microscope (SEM) or atomic force microscopy (AFM) measurement.

Accordingly, in an embodiment, to determine one or more substrate measurement recipes that would yield an accurate measurement of the desired process parameter (e.g., overlay) and/or that yields measurement values of the desired process parameter that is robust to process variability, a plurality of substrate measurement recipes can be evaluated against one or more performance indicators to identify such one or more accurate and/or robust substrate measurement recipes.

Figure 14:
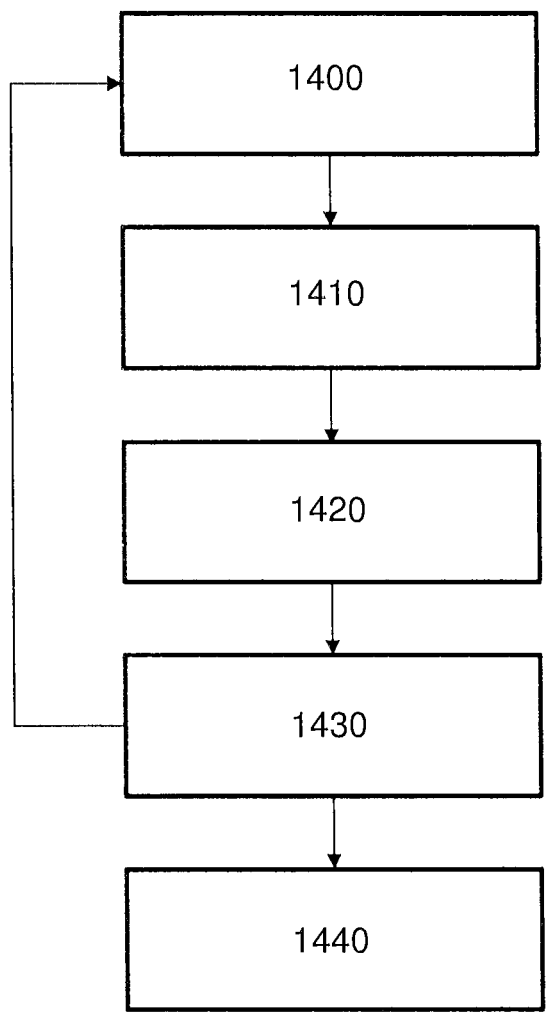
FIG. 14 is a flowchart of steps of a method according to an embodiment.

Referring to FIG. 14, an embodiment of a method to determine one or more substrate measurement recipes that would yield an accurate measurement of the desired process parameter (e.g., overlay) and/or that yields measurement values of the desired process parameter that is robust to process variability is schematically depicted. In this example method, a plurality of different metrology targets are each evaluated against a plurality of different values of measurement beam wavelength (i.e., the wavelengths available from an inspection apparatus that would be used to measure the target) and a plurality of different values of polarization (i.e., the polarizations available from the inspection apparatus that would be used to measure the target); each particular combination of target, wavelength and polarization corresponding to a particular substrate measurement recipe. However, the method is not so limited. For example, the method can be used to evaluate other or additional parameters than wavelength and polarization. As another example, the method can be used to evaluate just a single target (e.g., against a plurality of different wavelengths and polarizations, against a plurality of different wavelengths for a single polarization, against a single wavelength for a plurality of different polarizations, etc.). As another example, the method can be used to evaluate a plurality of targets against a plurality of different wavelengths for a single polarization. As another example, the method can be used to evaluate a plurality of targets against a plurality of different polarizations for a single wavelength.

Further, while various steps are shown in sequence, they need not necessarily be performed in that sequence. Further, all steps need not be performed. For example, one or more of the step may be performed. So, any combination selected from the steps can be performed.

At 1400, a first analysis of data for a single target against a plurality of different wavelengths and for a plurality of different polarizations (in this case, two polarizations) is performed. The data can be obtained experimentally or obtained from production measurements using the target. For example, a plurality of instances of a target under consideration can be printed across a substrate using the patterning process for which the target will be used and then each instance measured with the applicable inspection apparatus at a plurality of different settings (e.g., different wavelengths, different polarizations, etc.).

A process parameter (e.g., overlay, alignment, focus) measurement resulting from using a substrate measurement recipe to measure a target may be simulated. In the simulation, one or more parameters of the measurement are determined using (e.g., provided by, or determined from) the parameters $r_i$ and/or $t_j$ of the substrate measurement recipe. For example, the interaction between the radiation and the target corresponding to the substrate measurement recipe can be determined from those parameters of the substrate measurement recipe by using, for example, a Maxwell solver and rigorous coupled-wave analysis (RCWA) or by other mathematical modelling. So, the measurement expected using the target and the associated substrate measurement recipe can be determined from the interaction. So, in certain circumstances, for example to determine targets that yield strong signals, the data can be obtained using a simulator of the measurement process; the simulator can mathematically derive how a particular target of particular characteristics (e.g., a target specified in terms of pitch, feature width, material types, etc.) would be measured using an inspection apparatus according to the measurement technique (e.g., diffraction-based overlay measurement) of the inspection apparatus by, for example, calculating the intensity that would be measured in a detector of, e.g., the apparatus of FIG. 7. To obtain robustness data, the simulator can introduce a perturbation within a certain range (e.g., an up to 10% change, an up to 5% change, an up to 2% change, an up to 1% change, or an up to 0.5% change) to mimic process variation (which can be extended across a substrate).

So, the experimental method or simulation can yield values for particular parameters or indicators such as OV, K, etc. using, for example, the formulas described above.

One such indicator is stack sensitivity (SS) (also consider as signal contrast). Stack sensitivity can be understood as a measure of how much the intensity of the signal changes as overlay changes because of diffraction between target (e.g., grating) layers. That is, in an overlay context, it detects the contrast between upper and lower periodic structure of an overlay target and thus represents a balance between diffraction efficiencies between the upper and lower periodic structure. It is thus an example measure of sensitivity of the measurement. In an embodiment, stack sensitivity is the ratio between intensity asymmetry and average intensity. In an embodiment, stack sensitivity can be formulated as SS=K $L/I_M$, wherein L is a user defined constant (e.g., in an embodiment, the value L is 20 nm and/or the value of the bias d) and $I_M$ is the mean intensity of the measurement beam diffracted by the target. In an embodiment, the stack sensitivity for a substrate measurement recipe should be maximized. However, it has been discovered that use of a substrate measurement recipe with maximum stack sensitivity may not be best. For example, a measurement beam wavelength for which stack sensitivity is maximum may correspond to low overlay sensitivity and poor process robustness.

Figure 15:
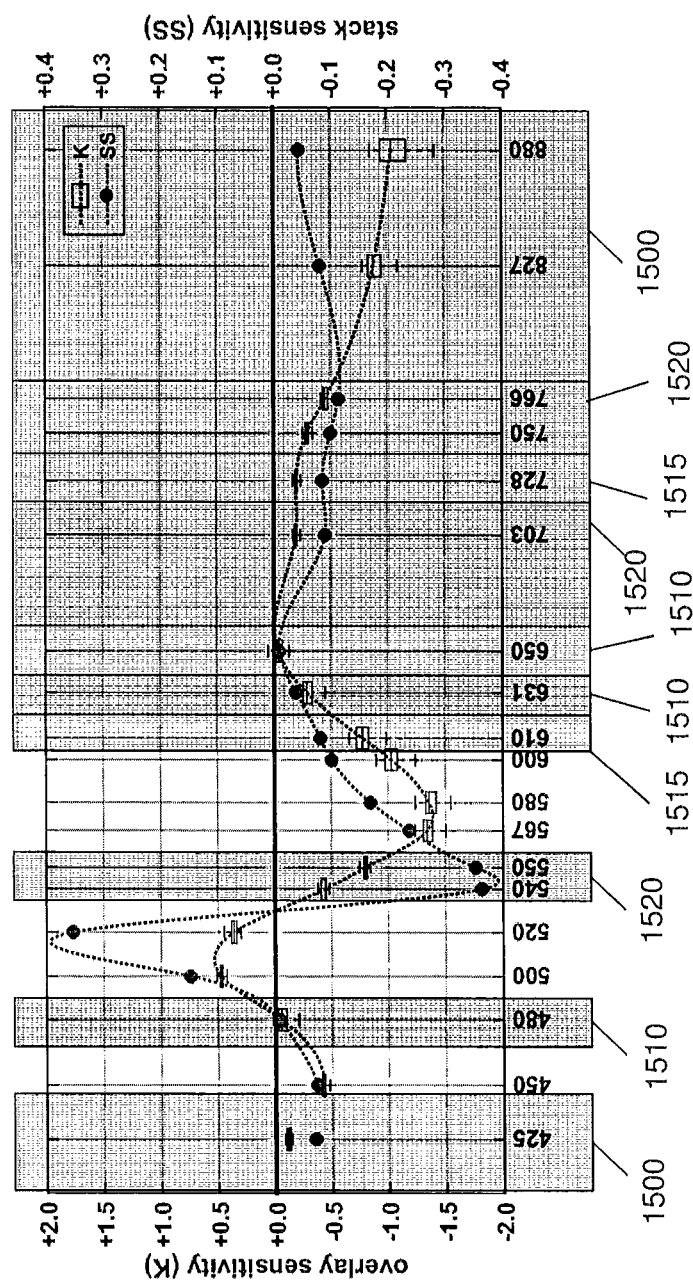
FIG. 15 is a graph of overlay sensitivity for a target for measurement at various wavelengths for a single polarization (in this case, linear X polarization)
Figure 16:
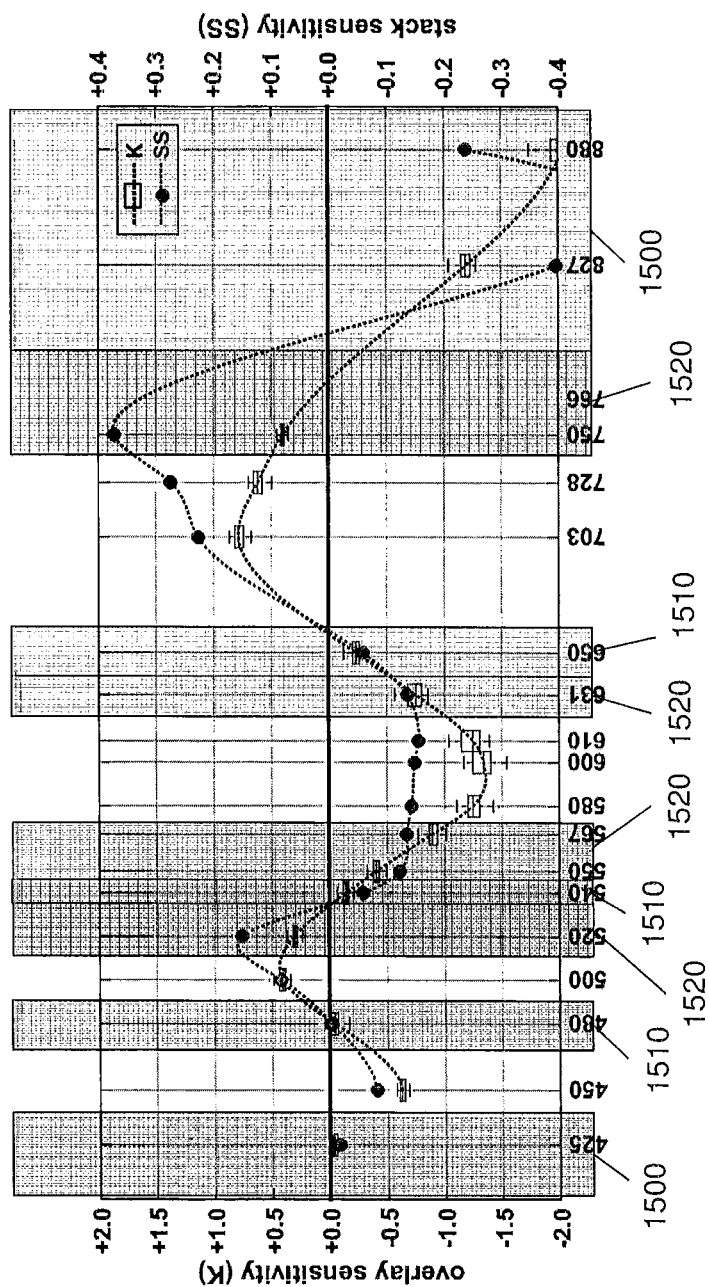
FIG. 16 is a graph of overlay sensitivity for a target for measurement at various wavelengths for a single polarization (in this case, linear Y polarization)

Examples of substrate measurement recipe data are presented in FIGS. 15 and 16. The data can represent a dependency of measurement data as a function of one or more substrate measurement recipe parameters, in particular one or more parameters of the measurement itself such as wavelength of the measurement beam. In an embodiment, the data can represent an oscillatory dependence of measured data (e.g., intensity obtained as field data (at an image plane) or pupil data (at pupil plane)) as a function of measurement radiation wavelength. FIG. 15 is an example graph of data for a target for measurement at various wavelengths for a single polarization (in this case, linear X polarization). A curve has been fitted through the data and so this representation can be called a swing curve. As will be appreciated, a graph need not be generated as just the data can be processed. FIG. 16 is a graph of data for the same target for measurement at various wavelengths for a different single polarization (in this case, linear Y polarization). In both FIGS. 15 and 16, stack sensitivity and overlay sensitivity are graphed for various measurement beam wavelengths. Further, while the polarizations here are linear X and Y polarization, it can be different or additional polarizations (such as left-handed elliptically polarized radiation, right-handed elliptically polarized radiation, etc.)

Using this data, one or more certain substrate measurement recipes are removed from consideration to result in a selection of a set of substrate measurement recipes for possible further consideration. In this case, the substrate measurement recipes share the same target but vary in terms of measurement radiation wavelength and measurement radiation polarization.

Now, initially, certain wavelengths can be eliminated because they are beyond the pitch/wavelength limit for that particular target. That is, the pitch of the target features and the measurement radiation wavelength are such that measurement at this combination would be ineffective. These one or more substrate measurement recipes are excluded in regions 1500.

A further aspect of this selection is to select those one or more substrate measurement recipes with a stack sensitivity (e.g., a mean stack sensitivity obtained from a plurality of instances of a target across a substrate (which can then be determined for a plurality of substrates)) that meets or crosses a threshold (i.e., within a certain range of stack sensitivity values). In an embodiment, the stack sensitivity should be maximized (but as discussed above, not at the expense of other indicators or parameters and moreover, there may be an upper limit on stack sensitivity discussed below that can affect robustness to process variation). For example, the one or more substrate measurement recipes with an absolute value of stack sensitivity of greater than or equal to 0.05 can be selected for further consideration. Of course, 0.05 need not be used. If the number is higher in this case, more measurement recipes would be excluded. So, the stack sensitivity number in this case is relatively low. So, those one or more substrate measurement recipes excluded by this aspect of the selection are marked as regions 1510 (where the regions roughly correspond to the wavelengths available by the inspection apparatus in this circumstance; the analysis as applied to the curve in FIGS. 15 and 16 would be more precise if a continuous wavelength range were available and the inspection apparatus can precisely and stably tune to any wavelength in the range).

An optional extra criteria is consideration of target sigma. Target sigma (TS) can be understood as the statistical variation of the measured parameter (e.g., overlay) for a plurality of measured pixels across a target. In theory, each pixel should be measured by a detector to read a same parameter value for a particular target. However, in practice, there can be variation among the pixels. In an embodiment, target sigma is in the form of a standard deviation or the form of variance. So, a low value of target sigma means a desirable low variation in the measured parameter across the target. A high value of target sigma (TS) can signal an issue in printing of the target (e.g., a misformed grating line), an issue of contamination (e.g., a significant particle on the target), an issue in measurement beam spot positioning, and/or an issue in measurement beam intensity variation across the target.

So, a further aspect of this selection can be to select those one or more substrate measurement recipes with a target sigma (e.g., a mean target sigma obtained from a plurality of instances of a target across a substrate (which can then be determined for a plurality of substrates)) that meets or crosses a threshold (i.e., within a certain range of target sigma values). In an embodiment, the target sigma should be minimized. For example, the one or more substrate measurement recipes with a target sigma of less than or equal to 10 nm can be selected for further consideration. Of course, 10 nm need not be used. If the number is lower in this case, more substrate measurement recipes would be excluded. So, the target sigma number in this case is relatively high. So, those one or more substrate measurement recipes excluded by this aspect of the selection are marked as regions 1515 (where the regions roughly correspond to the wavelengths available by the inspection apparatus in this circumstance).

Further, referring to discussion in respect of equations (4) and (5) above, to reduce the measured error in overlay, a set of measurement conditions (e.g., target selection, measurement beam wavelength, measurement beam polarization, etc.) should be selected with a large overlay sensitivity K. So, a further aspect of this selection is to select those one or more substrate measurement recipes with an overlay sensitivity (e.g., a mean overlay sensitivity obtained from a plurality of instances of a target across a substrate (which can then be determined for a plurality of substrates)) that meets or crosses a threshold (i.e., within a certain range of overlay sensitivity values). In an embodiment, the overlay sensitivity should be maximized for a substrate measurement recipe. For example, the one or more substrate measurement recipes having an absolute value of overlay sensitivity within a range of the absolute value of highest overlay sensitivity can be selected for further consideration. For example, the range can be within 35%, within 30%, within 25%, within 20%, within 15% or within 10% of the highest overlay sensitivity value. For example, the one or more substrate measurement recipes within a range from a local minima or maxima of the overlay sensitivity values can be selected. For example, the range can be within 35%, within 30%, within 25%, within 20%, within 15%, or within 10% of the local minima or maxima. Of course, different ranges can be used. The higher the range, the more substrate measurement recipes retained. So, those one or more substrate measurement recipes excluded by this aspect of the selection are marked as regions 1520 (where the regions roughly correspond to the wavelengths available by the inspection apparatus in this circumstance).

As a result, one or more substrate measurement recipes should remain (of course, if no substrate measurement recipes remain then one or more other substrate measurement recipe parameters may need to be modified, e.g., one or more parameters of the target itself). In this example (where the inspection apparatus offers certain wavelengths), the remaining substrate measurement recipes are those wherein the target is measured with linear X polarization radiation at 450 nm, 500 nm, 520 nm, 567 nm, 580 nm, and 600 nm wavelength and wherein the target is measured with linear Y polarization radiation at 450 nm, 500 nm, 580 nm, 600 nm, 610 nm, 703 nm and 728 nm. At this point, the one or more selected substrate measurement recipes could be output and used in a measurement operation and should yield relatively strong measurement signals.

At 1410, a plurality of selected substrate measurement recipes from 1400 can be further refined to select one or more substrate measurement recipes having increased measurement accuracy. In an embodiment, one or more further thresholds can be applied using one or more various performance indicators.

In an embodiment, a subset of one or more substrate measurement recipes can be selected by evaluating stack sensitivity against a further more restrictive threshold. For example, the one or more substrate measurement recipes with an absolute value of stack sensitivity of greater than or equal to 0.13 and less than or equal to 0.8 can be selected for further consideration. Of course, 0.13 and 0.8 need not be used. An upper limit (0.8 in this example) is used to avoid selecting a substrate measurement recipe with too high of a stack sensitivity, which can tend to be not robust to process variation.

In an embodiment, a subset of one or more substrate measurement recipes can be selected by evaluating target sigma against a further more restrictive threshold. For example, the one or more substrate measurement recipes with a target sigma of less than or equal 4 nm can be selected for further consideration. Of course, 4 nm need not be used.

In an embodiment, a subset of one or more substrate measurement recipes can be selected by evaluating target sigma variation against a threshold. The target sigma variation corresponds to a statistical variation of target sigma for a plurality of instances of the target across the substrate. In an embodiment, target sigma variation is in the form of a standard deviation or in the form of variance. In an embodiment, the target sigma variation is in the form of standard deviation and target sigma $3\sigma$ can be evaluated against a threshold. For example, the one or more substrate measurement recipes with a target sigma $3\sigma$ of less than or equal 1 nm can be selected for further consideration. Of course, 1 nm need not be used. In an embodiment, target sigma variation should be minimized.

In an embodiment, a subset of one or more substrate measurement recipes can be selected by evaluating a stack difference parameter against a threshold. In an embodiment, the stack difference parameter comprises grating imbalance (GI). So, for example, a subset of one or more substrate measurement recipes can be selected by evaluating grating imbalance (GI) (e.g., a mean grating imbalance or a variation (e.g., variance, standard deviation, etc.) of grating imbalance, obtained from a plurality of instances of a target across a substrate (which can then be determined for a plurality of substrates)) against a threshold. For example, the one or more substrate measurement recipes with a grating imbalance of less than or equal 0.05 or 5% can be selected for further consideration. Of course, 0.05 or 5% need not be used. In an embodiment, the stack difference parameter is minimized.

In an embodiment, a subset of substrate measurement recipes can be selected by evaluating a self-referential indicator (obtained from a plurality of instances of a target across a substrate (which can then be determined for a plurality of substrates)) against a threshold. In an embodiment, the self-referential indicator is, or involves, a self-reference performance parameter (e.g. overlay) obtained using the versus $A_-$ analysis described in PCT patent application publication no. WO 2015/018625, which is incorporated herein in its entirety by reference.

The $A_+$ versus $A_-$ analysis in the present context would mean evaluating the substrate measurement recipes for a plurality of instances of a target having a periodic structure with a positive bias ($A_+$) and a periodic structure with a negative bias ($A_-$). So, for overlay as the performance parameter, $A_+$ and $A_-$ is determined for each of the substrate measurement recipes and for each instance of the target and the determined values of $A_+$ are evaluated against the determined values of $A_-$ to yield a fitting through such data and a value related to that fitting corresponds to the "true" overlay for an instance of a target. This would be repeated for each instance of the target to yield a plurality of values of the self-reference performance parameter. In an embodiment, those plurality of values are averaged to yield an average (e.g., mean) "true" overlay across the substrate (where it is assumed that each instance of target is intended to have the same overlay).

Figure 17:
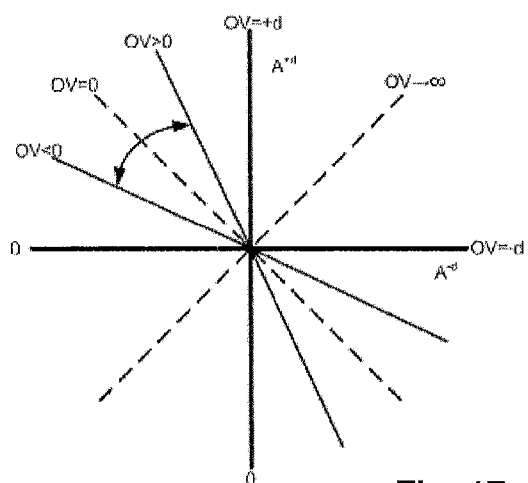
FIG. 17 is a plot of $A_+$ versus $A-$ for overlay gratings that have no feature asymmetry.

FIG. 17 is an example plot of $A_+$ versus $A_-$ for overlay gratings that have no feature asymmetry, such that the only asymmetry present is the asymmetry due to the bias and overlay, to show the fitting. In this case, the relation between $A_+$ and $A_-$ lies on a straight line through the origin (because no feature asymmetry is assumed). The corresponding $A_+$ versus $A_-$ data points for all the substrate measurement recipes lie on this line. The slope of this line (which is the fitting) is related to the "true" overlay. FIG. 17 shows a dotted line labelled OV=0, which is a line indicating zero overlay and having a slope of −1, a dotted line labelled $OV_{\infty}$, which is a line having a slope of +1 and is indicative of overlay approaching infinity, a solid line labelled OV<0, which is a line having a slope less than −1 and is indicative of overlay less than zero, and a solid line labelled OV>0, which is a line having a slope greater than −1 and is indicative of overlay greater than zero. Additionally, it can be seen that overlay equal to +d, where d is the grating bias, would result in a plotted line along the y-axis; and overlay equal to −d would result in a plotted line along the x-axis.

So, $A_+$ versus $A_-$ regression can yield a "true" overlay as it would be without a contribution attributable to feature asymmetry, by determination of the slope of a fitted line through the data set, the line not necessarily being fitted through the origin. Optionally, feature asymmetry could be determined via an offset of the fitted line from the origin (e.g., an intercept term).

Further, an actual measured value of overlay can be determined for each of the instances of the target as well as for each substrate measurement recipe (where it is assumed that each instance of target is intended to have the same overlay). These values can be statistically processed to yield an average and a statistical variation (e.g., a standard deviation) of overlay for a particular substrate measurement recipe.

Then, the self-referential indicator can be a comparison between the true "overlay" and the measured value of overlay for a particular substrate measurement recipe. In an embodiment, the self-referential indicator is a difference between the average "true overlay" and the average measured value of overlay plus 3 standard deviations, which can be evaluated against a threshold (e.g., the substrate measurement recipe will be selected if the self-referential indicator in this case is less than or equal to 3 nm, although a different value than 3 nm can be used). Thus, this self-referential indicator is effectively a residual fingerprint across the substrate. In an embodiment, the self-referential indicator should be minimized.

So, in effect, this technique involves fitting the asymmetries of periodic structures (e.g., biased overlay gratings) detected using a number of different substrate measurement recipes across the substrate to produce a self-reference fingerprint of a "true" process parameter (e.g., overlay.) The self-reference "true" process parameter (e.g., overlay) is then compared with a measured value of the process parameter (e.g., overlay) of one or more substrate measurement recipes to identify which one or more substrate measurement recipe yields results close to the self-reference fingerprint to help assure accuracy of measurement using those one or more substrate measurement recipes.

Figure 18:
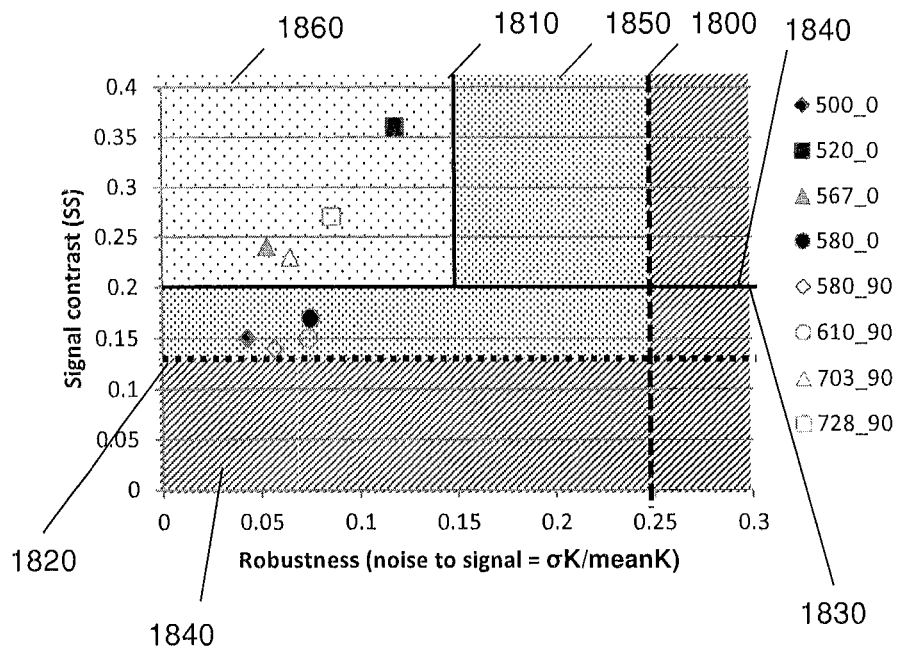
FIG. 18 is a graph of stack sensitivity SS versus a robustness indicator for a plurality of substrate measurement recipes.

So, at 1410, a plurality of substrate measurement recipes from 1400 can be further refined to select one or more substrate measurement recipes, such as those one or more substrate measurement recipes shown in FIG. 18 wherein the target is measured with linear X polarization radiation at 500 nm, 520 nm, 567 nm, and 580 nm wavelength and wherein the target is measured with linear Y polarization radiation at 580 nm, 610 nm, 703 nm and 728 nm. At this point, the one or more selected substrate measurement recipes could be output and used in a measurement operation and should yield relatively accurate measurement results.

At 1420, a plurality of the selected substrate measurement recipes from 1410 can be further refined to select one or more substrate measurement recipes having increased robustness to process variation. In an embodiment, one or more further thresholds can be applied using one or more various performance indicators.

In an embodiment, a subset of one or more substrate measurement recipes can be selected by evaluating a robustness indicator against a threshold. In an embodiment, the robustness indicator can be understood as a measure of the variation of a parameter or indicator that represents a sensitivity, across a substrate for a plurality instances of the target located across the substrate (which can then be determined for a plurality of substrates). In an embodiment, the robustness indicator can be understood as a measure of the variation of overlay sensitivity across a substrate for a plurality instances of the target located across the substrate (which can then be determined for a plurality of substrates). In an embodiment, the robustness indicator takes the form of $\sigma K/|K_M|$, wherein $\sigma K$ is the statistical variation (e.g., standard deviation, variance) in overlay sensitivity K across the substrate and $|K_M|$ is the average (e.g., mean) of the absolute value of the overlay sensitivity K across the substrate.

Referring to FIG. 18, a graph of stack sensitivity SS versus a robustness indicator for the plurality of substrate measurement recipes selected in 1410 is depicted. So, in an embodiment, a threshold can applied to the robustness indicator and as well to the stack sensitivity. In this embodiment, several thresholds are depicted which in effect create several zones of robustness.

In an embodiment, a first threshold is a threshold 1800 for the robustness indicator, e.g., 0.25 as shown in FIG. 18. So, any substrate measurement recipe having a value of the robustness indicator of less than or equal 0.25 is considered for selection. As shown in FIG. 18, all substrate measurement recipes selected in 1410 qualify for selection as being a substrate measurement recipe for use in, for example, production use.

In an embodiment, a second threshold is a threshold 1810 for the robustness indicator, e.g., 0.15 as shown in FIG. 18. So, any substrate measurement recipe having a value of the robustness indicator of less than or equal 0.15 is considered for selection. As shown in FIG. 18, all substrate measurement recipes selected in 1410 qualify for selection as being a substrate measurement recipe for use in, for example, production use.

In an embodiment, a third threshold is a threshold 1820 for the stack sensitivity, e.g., 0.13 as shown in FIG. 18. So, any substrate measurement recipe having a value of the stack sensitivity of greater than or equal 0.13 is considered for selection. As noted above, in 1410, such a selective threshold of stack sensitivity may have already been previously applied and so all measurement recipes selected in 1410 may already qualify. As shown in FIG. 18, all substrate measurement recipes selected in 1410 qualify for selection as being a substrate measurement recipe for use in, for example, production use.

In an embodiment, a fourth threshold is a threshold 1830 for the stack sensitivity, e.g., 0.2 as shown in FIG. 18. So, any substrate measurement recipe having a value of the stack sensitivity of greater than or equal 0.2 is considered for selection. As shown in FIG. 18, only a subset of the substrate measurement recipes selected in 1410 qualify for selection under this constraint as being a substrate measurement recipe for use in, for example, production use.

And, so, the first to fourth thresholds define regions for selection of one of more substrate measurement recipes. A first region 1840 which is outside the first and third thresholds can define an area where if a substrate measurement recipe is located in that area, it is not acceptable for further consideration. A second region 1850 can be defined as outside the second and fourth thresholds but within the first and third thresholds. If a substrate measurement recipe is located in that region 1850, it may still be acceptable for further consideration. And, a third region 1860 can be defined as being within the second and fourth thresholds. If a substrate measurement recipe is located in that region 1850, it is considered acceptable for further consideration. As seen, in FIG. 18, select substrate measurement recipes are within region 1850, specifically substrate measurement recipes wherein the target is measured with linear X polarization radiation at 520 nm and 567 nm wavelength and wherein the target is measured with linear Y polarization radiation at 703 nm and 728 nm. A further refinement in obtaining an accurate value of a parameter, such as overlay, is using the combination of the wavelengths from region 1860, for example.

Optionally, one or more substrate measurement recipes are selected with a stack sensitivity of at least 0.25 and less than or equal to 0.5.

In an embodiment, a robustness indicator can take the form of $\sigma SS/|SS_M|$, wherein $\sigma SS$ is the statistical variation (e.g., standard deviation, variance) in stack sensitivity SS across the substrate (which can then be determined for a plurality of substrates) and $|SS_M|$ is the average (e.g., mean) of the absolute value of the stack sensitivity SS across the substrate.

So, at 1420, the substrate measurement recipes selected in 1410 can be further refined to select one more substrate measurement recipes, such as the substrate measurement recipes wherein the target is measured with linear X polarization radiation at 520 nm and 567 nm wavelength and wherein the target is measured with linear Y polarization radiation at 703 nm and 728 nm. At this point, the one or more selected substrate measurement recipes could be output and used in a measurement operation and should yield measurement results relatively robust to process variation.

At 1430, a plurality of substrate measurement recipes from 1420 can be further refined to select substrate measurement recipes. In an embodiment, further thresholds can be applied using one or more various performance indicators.

In an embodiment, the substrate measurement recipes from 1420 can be re-evaluated against the respective swing curve(s) (or its associated data). In particular, it can be evaluated whether one or more indicators (such as overlay sensitivity and/or stack sensitivity) are stable. In an embodiment, the derivative of the indicator can be evaluated. For example, a substrate measurement recipe can be considered stable (and selected) if the absolute value of the derivative of the indicator is less than or equal to 5, less than or equal to 1, less than or equal to 0.5, or less than or equal to 0.1. In an embodiment, the derivative can be evaluated over a range (e.g., within 10%, within 5%, or within 1%) from a value of a parameter (e.g., wavelength) of the substrate measurement recipe to see whether the derivative (e.g., the individual values in the range, the average of the derivative in the range, etc.) crosses the threshold.

So, as an example, referring back to FIG. 15 and taking the selected substrate measurement recipe from 1420 of the target measured with linear X polarization radiation at 520 nm, it can be seen that the derivative of the stack sensitivity for that substrate measurement recipe is high (e.g., greater than 1). Moreover, the derivative of the stack sensitivity over a range of about 518 nm to 525 nm around 520 nm of the substrate measurement recipe also has a high derivative (e.g., greater than 1 on average and individually). So, this substrate measurement recipe can be excluded even though the derivative for overlay sensitivity may be acceptable.

In contrast, it can be seen, referring back to FIG. 15 and taking the selected substrate measurement recipe from 1420 of the target measured with linear X polarization radiation at 567 nm, it can be seen that the derivative of the stack sensitivity for that substrate measurement recipe is relatively low. Similarly, the derivative of the overlay sensitivity is also relatively low. And so, this substrate measurement recipe can be selected.

In an embodiment, the derivative values of two or more indicators should be the same or within a certain range (e.g., within 5%, within 10%, within 20%, or within 30%) of each other. For example, if the derivative for one indicator (e.g., stack sensitivity) is 1, the other indicator should have a derivative within the range of 0.95 to 1.05 (for a 5% range) or within the range of 0.9 and 1.1 (for a 10% range) and so on.

Further, at 1430, it is shown that optionally one or more the steps 1400, 1410, 1420 and/or 1430 can be repeated for a different set of substrate measurement recipe parameters that is maintained across the plurality of substrate measurement recipes evaluated in steps 1400, 1410, 1420 and/or 1430. For example, in the examples presented above, a particular target type was evaluated against varying wavelength and polarization. So, for example, the different set can be a different type of target (e.g., different in one or target parameters as discussed above such as pitch, feature width, material, etc.), which is then evaluated in steps 1400, 1410, 1420 and/or 1430 for, for example, varying wavelength and polarization.

In an embodiment, the repeating can be triggered if there isn't at least one substrate measurement recipe identified from steps 1400, 1410, 1420 and/or 1430. That is, one or more new different sets of substrate measurement recipe parameters that are each maintained across the plurality of substrate measurement recipes evaluated in steps 1400, 1410, 1420 and/or 1430 can be provided by a user or calculated (e.g., by an interpolation or extrapolation method from a previous set).

In an embodiment, the repeating can be performed for a plurality of selected different sets of substrate measurement recipe parameters that is maintained across the plurality of substrate measurement recipes evaluated in steps 1400, 1410, 1420 and/or 1430. One or more sets of the different sets of substrate measurement recipe parameters that are each maintained across the plurality of substrate measurement recipes evaluated in steps 1400, 1410, 1420 and/or 1430 can be provided by a user or calculated (e.g., by an interpolation or extrapolation method from a previous set). The result of the repeating can be identification of just one substrate measurement recipe. Or, the result can be identification of a plurality of substrate measurement recipes, e.g., a plurality of substrate measurement recipes associated with one set (e.g., particular target type) or at least one substrate measurement recipe for each of two or more sets (e.g., two or more target types) among the plurality of sets (e.g., plurality of different target types).

So, at 1430 (whether there is repetition as discussed above or not), the one or more selected substrate measurement recipes could be output and used in a measurement operation and should yield relatively accurate and robust measurement results.

At 1440, where there is a plurality of substrate measurement recipes, the substrate measurement recipes can then be ranked together or with respect to each set. The top substrate measurement recipe or a substrate measurement recipe within the top 5 or within the top 10 can then be output and used in a measurement operation and should yield relatively accurate and robust measurement results.

In an embodiment, the ranking can be based on a matching indicator that identifies the extent to which a process parameter (e.g., overlay) as measured using the substrate measurement recipe matches the value of the process parameter for a functional device pattern on a substrate. That is, in an embodiment, the matching indicator provides a correlation between the parameter as measured using the target of the substrate measurement recipe and actual parameter value of a functional device pattern (for which the target is intended to determine the value of the parameter). This can be determined, for example, through correlating measurements made using the substrate measurement recipe and measured values of the functional device pattern measured using, for example, a SEM.

In an embodiment, the ranking can be based on any one or combination of of the indicators or parameters identified above. For example, the ranking can be based on stack sensitivity (e.g., stack sensitivity within the range of 0.35 to 0.40) or a robustness indicator (e.g., $\sigma K/|K_M|$ of less than 0.04). In an embodiment, the ranking can be based on a combination of two or more of the indicators or parameters identified above with an optional different weighting of the indicators or parameters in the combination.

So, at 1440, the one or more selected substrate measurement recipes could be output and used in a measurement operation and should yield relatively accurate and robust measurement results.

In an embodiment, one or more of the parameters or indicators (e.g., stack difference parameter) can be used to derive, for example, a corrected measurement of a parameter of interest, such as overlay, CD, focus, dose, etc., made using a target. The corrected measurements naturally may be used in creating, qualifying, verifying, etc., for example, devices by a patterning process. Additionally or alternatively, the one or more of the parameters or indicators (or a parameter derived from the stack difference parameter, such as a corrected measurement) can be used in the (re-)design of the substrate measurement recipe (e.g., in the target, such as making a change to a layout of the design), can be used in the process of forming a target (e.g., making a change in material, a change in a printing step or condition, etc.), can be used in formulation of the measurement conditions (e.g., make a change in the optical measurement formulation in terms of wavelength, polarization, illumination mode, etc. of the measurement beam), etc.

In an embodiment, one or more of the parameters or indicators (e.g., stack difference parameter) can be used in a simulation of optical measurement of the target to derive, for example, a corrected simulated measurement of a parameter of interest, such as overlay, CD, focus, dose, etc. For example, one or more of the parameters or indicators (e.g., stack difference parameter) can be used to calibrate a mathematical model, for example, used to simulate at least part of the patterning process, simulate at least part of the measurement process, etc.

In an embodiment, there is provided a method of identifying desirable target designs and desirable combinations of target design and measurement parameters. Once identified, the combination(s) can be used in performing metrology measurements. As noted above, target designs may be varied in a number of ways. There may be variation in one or more parameters such as critical dimension, sidewall angle, or pitch, for example. So, a number of candidate target designs may be evaluated, each showing variation in one or more of these parameters. Further, measurement parameters may be varied in terms of wavelength, polarization, etc.

So, in an embodiment, a parameter space of the various substrate measurement recipes can be sampled to identify candidate substrate measurement recipes and then put through one or more of the methods described herein to identify whether the substrate measurement recipe is suitable. Interpolation and/or extrapolation of substrate measurement recipe parameters (e.g., based on the results of the evaluations herein) can be used to choose substrate measurement recipe candidates. So, numerous substrate measurement recipes may be evaluated, each recipe showing variation in one or more applicable parameters.

So, in an embodiment, there is provided a method of optimum selection of a substrate measurement recipe for metrology. In an embodiment, the methodology yields an accurate and robust substrate measurement recipe. In an embodiment, the optimization is performed using measured data. In an embodiment, the optimization is performed using simulated data. In an embodiment, the optimization is performed using both simulated and measured data.

So, in an embodiment, a substrate measurement recipe can be optimized in terms of one or more of the indicators or parameters (e.g., stack difference, overlay sensitivity, etc.). Some or all of the parameters of the substrate measurement recipe may be adjusted in the optimization. For example, one or more parameters of the target and/or one or more parameters of the measurement may be adjusted. The optimization may use a cost function that represents a metric representing one or more of the indicators (e.g., a plurality of the indicators). Each applicable indicator can be, for example, maximized or minimized as noted above, subject to any applicable constraints.

In an optimization of process or apparatus, a figure of merit can be represented as a cost function. The optimization process boils down to a process of finding a set of parameters (design variables) of the system or process that optimizes (e.g., minimizes or maximizes) the cost function. The cost function can have any suitable form depending on the goal of the optimization. For example, the cost function can be weighted root mean square (RMS) of deviations of certain characteristics of the process and/or system with respect to the intended values (e.g., ideal values) of these characteristics; the cost function can also be the maximum of these deviations (i.e., worst deviation). The design variables can be confined to finite ranges and/or be interdependent due to practicalities of implementations of the process and/or system. In the case of a measurement process, the constraints are often associated with physical properties and characteristics of the hardware, a measurement step and/or a patterning step, such as tunable ranges of hardware and/or target manufacturability design rules.

As an example, a cost function may be expressed as $$CF(z_1, z_2, \ldots, z_N) = \sum_{p=1}^{P} w_p f_p^2(z_1, z_2, \ldots, z_N) \quad (9)$$

wherein $(z_1, z_2, \ldots, z_N)$ are N design variables or values thereof. $f_p(z_1, z_2, \ldots, z_N)$ can be a function of the design variables $(z_1, z_2, \ldots, z_N)$, such as a metric representing one or more of the indicators or parameters (e.g., stack difference, overlay sensitivity, etc.) corresponding to a particular substrate measurement recipe, for a set of values of the design variables of $(z_1, z_2, \ldots, z_N)$. So more generally, $f_p(z_1, z_2, \ldots, z_N)$ can be a metric characterizing the performance (e.g., sensitivity, robustness (namely how much the result of the measurement using a substrate measurement recipe varies under perturbation), etc.) of an associated substrate measurement recipe.

While $CF(z_1, z_2, \ldots, z_N)$ can correspond to a single $f_p(z_1, z_2, \ldots, z_N)$, in an embodiment, $CF(z_1, z_2, \ldots, z_N)$ is a combination of $f_p(z_1, z_2, \ldots, z_N)$ wherein each $f_p (z_1, z_2, \ldots, z_N)$ characterizes one or more selected from: stack sensitivity, overlay sensitivity, self-referential indicator, robustness indicator, target sigma, etc. Each parameter or indicator can be optimized as discussed above (e.g., stack sensitivity is maximized, overlay sensitivity is maximized, etc.) and can be subject to one or more constraints (e.g., certain floors). $w_p$ is a weight constant associated with $f_p (z_1, z_2, \ldots, z_N)$ and of course, could have different values for different $f_p(z_1, z_2, \ldots, z_N)$. Of course, $CF(z_1, z_2, \ldots, z_N)$ is not limited to the form in Eq. 1. $CF(z_1, z_2, \ldots, z_N)$ can be in any other suitable form.

Thus, in an embodiment, the cost function can include one or more performance indicators or parameters of both accuracy and robustness. In an embodiment, the cost function can be the same, or similar in form to, the following:

$$\text{Cost Function} = \sqrt{(W1 * PI_{accuracy})^2 + (W2 * PI_{robustness})^2} + \quad (10)$$

Penalty function $(PI_{accuracy}, PI_{robustness})$ wherein $PI_{accuracy}$ is one or more performance indicators or parameters for accuracy (e.g., overlay sensitivity), $PI_{robustness}$ is one or more performance indicators or parameters for robustness (e.g., robustness indicator), and W1 and W2 are weighting coefficients. With this format, both accuracy and robustness are co-optimized mathematically. If better accuracy is desired, then W1 would be larger than W2.

In an embodiment, the design variables $(z_1, z_2, \ldots, z_N)$ comprise one or more characteristics/parameters of the target. For example, the design variables can include one or more geometric characteristics (e.g., pitch of features of a periodic structure of the target, CD of a feature of a periodic structure of the target (e.g., the widths of the exposed portions and/or unexposed portions), segmentation of individual features of a periodic structure of the pattern, shape of at least part of a periodic structure, length of a periodic structure or of a feature of the periodic structure, etc.) and/or one or more materials properties (e.g., refractive index of a layer of the target, extinction coefficient of a layer of the target, etc.). In an embodiment, the design variables include a plurality of characteristics/parameters of the target. In an embodiment, the design variables can include any adjustable parameters of the measurement itself. For example, the design variables $(z_1, z_2, \ldots, z_N)$ may include wavelength, polarization, and/or pupil shape specified in the substrate measurement recipe.

In an embodiment, multiple sets of initial values of design variables ("seeds") can be introduced and evaluated/optimized. For example, there can be less than or equal to 500, less than or equal 200, less than or equal to 100 seeds, or less than or equal to 50 seeds.

The optimization may be repeated by starting with different seeds. The initial values may be random (the Monte Carlo method), or may be supplied by a user. The seeds may be evenly spaced in a value space spanned by the design variables. Starting the optimization with different seeds reduces the chance of being trapped to a local extremum.

Further, to take advantage of parallel computation, multiple different seeds can be introduced and evaluated/optimized independently to increase the chance of finding an optimum. Thus, multiples seeds can be used derive respective optimums, from which best candidates can be chosen.

The design variables may have constraints, which can be expressed as $(z_1, z_2, \ldots, z_N) \in Z$, where $Z$ is a set of possible values of the design variables. The constraints can be, for example, on one or more geometric characteristics of the target design (e.g., one or more design rules that specify that a particular geometric feature of the final target design must fall within a boundary set by an applicable process design rule) and/or, for example, a dimension requirement set by a measurement apparatus used to measure the target with the measurement recipe.

Further, in an embodiment, a penalty function is introduced to automatically limit the cost function within a desired range of the one or more metrics. For example, one possible constraint on the design variables may be that the performance (e.g., accuracy, robustness, etc.) associated with measurement of the target design according to its associated recipe may not, or must, cross an associated threshold. Without such a constraint, the optimization may yield a substrate measurement recipe that yields too weak a signal or that is too unstable. In an embodiment, the penalty function comprises a constraint on a characteristic of the target (e.g., a geometric characteristic of the target). For example, it could constrain stack sensitivity to, for example, between 0.2 and 0.8. In that case, in an embodiment, a penalty function for stack sensitivity can be, or comprise, the form of: $P(x)=c*((max(0,0.2-x))^2+(max (0,x-0.8))^2)$, wherein c is a constant and the values 0.2 and 0.8 can be different. However, the usefulness of constraints and the penalty function should not be interpreted them as being a necessity.

The optimization process therefore is to find a set of values of the one or more design variables, under the optional constraints $(z_1, z_2, \ldots, z_N) \in Z$ and subject to an optional penalty function, that optimize the cost function, e.g., to find:

$$(\tilde{z}_1, \tilde{z}_2, \ldots, \tilde{z}_N) = \arg\min_{(z_1, z_2, \ldots, z_N) \in Z} CF(z_1, z_2, \ldots, z_N) \quad (11)$$

Figure 19:
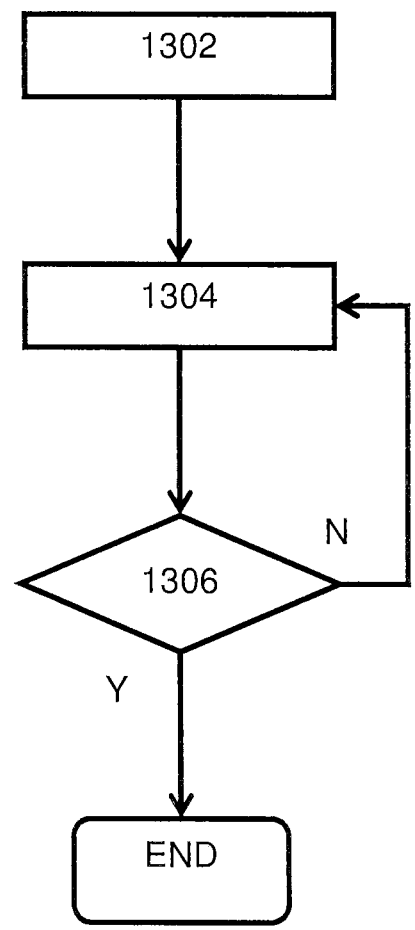
FIG. 19 is a flow diagram illustrating aspects of an example methodology of joint optimization/co-optimization.

A general method of optimizing, according to an embodiment, is illustrated in FIG. 19. This method comprises a step 1302 of defining a multi-variable cost function of a plurality of design variables as discussed above. For example, in an embodiment, the design variables comprise one or more characteristics/parameters of the target design and/or of the measurement. In step 1304, the design variables are simultaneously adjusted so that the cost function is moved towards convergence. In step 1306, it is determined whether a predefined termination condition is satisfied. The predetermined termination condition may include various possibilities, e.g., one or more selected from: the cost function is minimized or maximized, as required by the numerical technique used, the value of the cost function is equal to a threshold value or crosses the threshold value, the value of the cost function reaches within a preset error limit, and/or a preset number of iterations is reached. If a condition in step 1306 is satisfied, the method ends. If the one or more conditions in step 1306 is not satisfied, the steps 1304 and 1306 are iteratively repeated until a desired result is obtained. The optimization does not necessarily lead to a single set of values for the one or more design variables because there may be a physical restraint. The optimization may provide multiple sets of values for the one or more design variables and allows a user to pick one or more sets.

The design variables can be adjusted alternately (referred to as alternate optimization) or adjusted simultaneously (referred to as simultaneous optimization). The terms "simultaneous", "simultaneously", "joint" and "jointly" as used herein mean that the design variables are allowed to change at the same time. The term "alternate" and "alternately" as used herein mean that not all of the design variables are allowed to change at the same time.

Figure 20:
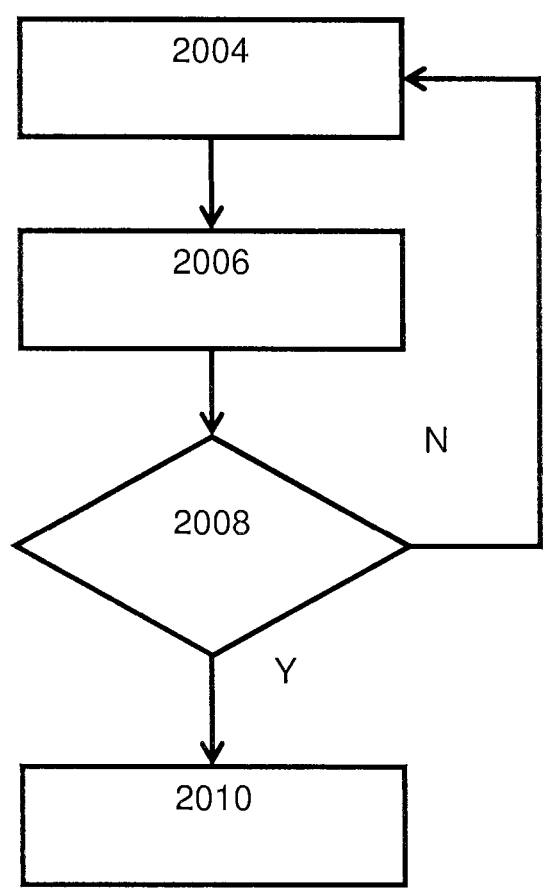
FIG. 20 shows an embodiment of a further optimization method, according to an embodiment.

In FIG. 19, the optimization of all the design variables is executed simultaneously. Such a flow may be called simultaneous flow or co-optimization flow. Alternately, the optimization of all the design variables is executed alternately, as illustrated in FIG. 20. In this flow, in each step, some design variables are fixed while other design variables are optimized to optimize the cost function; then in the next step, a different set of variables are fixed while the others are optimized to minimize or maximize the cost function. These steps are executed alternately until convergence or a certain terminating condition is met. As shown in the non-limiting example flowchart of FIG. 20, in step 2004, where a first group of design variables (e.g., one or more parameters of the target design) are adjusted to minimize or maximize the cost function while a second group of design variables (e.g., one or more other parameters of the target or one more parameters of the measurement) are fixed. Then in the next step 2006, the second group of the design variables is adjusted to minimize or maximize the cost function while the first group of design variables are fixed. These two steps are executed alternately, until a certain terminating condition is met in step 2008. One or more various termination conditions can be used, such as the value of the cost function becomes equal to a threshold value, the value of the cost function crosses the threshold value, the value of the cost function reaches within a preset error limit, a preset number of iterations is reached, etc. Finally the output of the optimization result is obtained in step 2010, and the process stops.

The optimization process described herein can beneficially enable stack tuning, such as altering one or more material layers, geometric characteristics, etc. of a metrology target to achieve an accurate and robust measurement result for a particular patterning process.

Figure 21:
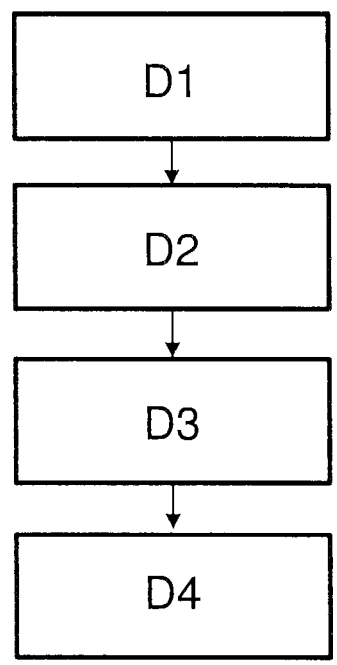
FIG. 21 is a flowchart illustrating a process in which the metrology target is used to monitor performance, and as a basis for controlling metrology, design and/or production processes.

FIG. 21 shows a flowchart illustrating a process in which the substrate measurement recipe is used to monitor performance, and as a basis for controlling metrology, design and/or production processes. In step D1, substrates are processed to produce product features and one or more metrology targets as described herein according to the applicable substrate measurement recipe. At step D2, patterning process parameter (e.g., overlay) values are measured using, if applicable, the one or more measurement parameters of the substrate measurement recipe and calculated using, e.g., the method of FIG. 6 or 10 and optionally, corrected using an asymmetry and/or stack difference parameter. At optional step D3, the measured patterning process parameter (e.g., overlay) value may be used (together with other information as may be available), to update the substrate measurement recipe (e.g., change a wavelength using a method as described herein). The updated metrology recipe is used for re-measurement of the patterning process parameter, and/or for measurement of the patterning process parameter on a subsequently processed substrate. In this way, the calculated patterning process parameter is improved in accuracy. The updating process can be automated if desired. In step D4, the patterning process parameter value is used to update a recipe that controls the lithographic patterning step and/or other process step in the device manufacturing process for re-work and/or for processing of further substrates. Again this updating can be automated if desired.

In an embodiment, there is provided a method comprising: evaluating a plurality of substrate measurement recipes for measurement of a metrology target processed using a patterning process, against stack sensitivity and overlay sensitivity; and selecting one or more substrate measurement recipes from the plurality of substrate measurement recipes that have a value of the stack sensitivity that meets or crosses a threshold and that have a value of the overlay sensitivity within a certain finite range from a maximum or minimum value of the overlay sensitivity.

In an embodiment, the method further comprises evaluating the plurality of substrate measurement recipes against target sigma and the selected one or more substrate measurement recipes have a value of the target sigma that meets or crosses a threshold. In an embodiment, the method further comprises evaluating the plurality of substrate measurement recipes against a robustness indicator representing statistical variation of a sensitivity parameter across the substrate, and the selected one or more substrate measurement recipes have a value of the robustness indicator that meets or crosses a threshold. In an embodiment, the robustness indicator represents a statistical variation of overlay sensitivity across the substrate divided by the average of absolute values of overlay sensitivity across the substrate. In an embodiment, the method further comprises evaluating the plurality of substrate measurement recipes against stack sensitivity and the selected one or more substrate measurement recipes have a value of the stack sensitivity that meets or crosses a more restrictive threshold. In an embodiment, the method further comprises evaluating the plurality of substrate measurement recipes against a stack difference parameter, the stack difference parameter representing an un-designed difference in physical configuration between adjacent periodic structures of the metrology target or between the metrology target and another adjacent target on the substrate, and the selected one or more substrate measurement recipes have a value of the stack difference parameter that meets or crosses a threshold. In an embodiment, the stack difference parameter comprises a periodic structure intensity imbalance. In an embodiment, the periodic structure intensity imbalance is a function of (i) the difference between the average intensity of measurement radiation from a first adjacent periodic structure or target and the average intensity of measurement radiation from a second adjacent periodic structure or target, and (ii) the addition of an average intensity of measurement radiation from the first adjacent periodic structure or target with an average intensity of measurement radiation from the second adjacent periodic structure or target. In an embodiment, the average intensity of measurement radiation from the first adjacent periodic structure or target corresponds to +n order radiation and the average intensity of measurement radiation from the second adjacent periodic structure or target corresponds to −n order radiation, wherein n is an integer greater than or equal to 1. In an embodiment, the method further comprises evaluating the plurality of substrate measurement recipes against a self-referential indicator that involves a process parameter value determined from a fitting among asymmetry data for a first periodic structure against asymmetry data for a second periodic structure, and the selected one or more substrate measurement recipes have a value of the self-referential indicator that meets or crosses a threshold. In an embodiment, the self-referential indicator involves a comparison of the process parameter value to at least an average of measured values of the process parameter. In an embodiment, the self-referential indicator involves a comparison of the process parameter value to a combination of an average of measured values of the process parameter and three times the standard deviation of the measured values of the process parameter. In an embodiment, the evaluating comprises computing a multi-variable cost function, the multi-variable cost function representing a metric characterizing the stack sensitivity and the overlay sensitivity, the metric being a function of a plurality of parameters from the substrate measurement recipe; and adjusting one or more of the parameters and computing the cost function with the adjusted one or more design parameters, until a certain termination condition is satisfied. In an embodiment, each of the substrate measurement recipes is different in terms of wavelength. In an embodiment, the evaluating comprises obtaining measurements of the metrology target using the inspection apparatus according to each of the substrate measurement recipes.

In an embodiment, there is provided a method comprising: evaluating a plurality of substrate measurement recipes for measurement of a metrology target on a substrate processed using a patterning process, against a robustness indicator representing statistical variation of a sensitivity parameter across the substrate; and selecting one or more substrate measurement recipes from the plurality of substrate measurement recipes that have the robustness indicator that meets or crosses a threshold. In an embodiment, the robustness indicator represents a statistical variation of overlay sensitivity across the substrate divided by the average of absolute values of overlay sensitivity across the substrate. In an embodiment, the method further comprises evaluating the plurality of substrate measurement recipes against stack sensitivity and the selected one or more substrate measurement recipes have a value of the stack sensitivity that meets or crosses a threshold. In an embodiment, the method further comprises evaluating the plurality of substrate measurement recipes against overlay sensitivity and the selected one or more substrate measurement recipes have a value of the overlay sensitivity within a certain finite range from a maximum or minimum value of the overlay sensitivity. In an embodiment, the method further comprises evaluating the plurality of substrate measurement recipes against a stack difference parameter, the stack difference parameter representing an un-designed difference in physical configuration between adjacent periodic structures of the metrology target or between the metrology target and another adjacent target on the substrate, and the selected one or more substrate measurement recipes have a value of the stack difference parameter that meets or crosses a threshold. In an embodiment, the stack difference parameter comprises a periodic structure intensity imbalance. In an embodiment, the periodic structure intensity imbalance is a function of (i) the difference between the average intensity of measurement radiation from a first adjacent periodic structure or target and the average intensity of measurement radiation from a second adjacent periodic structure or target, and (ii) the addition of an average intensity of measurement radiation from the first adjacent periodic structure or target with an average intensity of measurement radiation from the second adjacent periodic structure or target. In an embodiment, the average intensity of measurement radiation from the first adjacent periodic structure or target corresponds to +n order radiation and the average intensity of measurement radiation from the second adjacent periodic structure or target corresponds to −n order radiation, wherein n is an integer greater than or equal to 1. In an embodiment, the method further comprises evaluating the plurality of substrate measurement recipes against a self-referential indicator that involves a process parameter value determined from a fitting among asymmetry data for a first periodic structure against asymmetry data for a second periodic structure, and the selected one or more substrate measurement recipes have a value of the self-referential indicator that meets or crosses a threshold. In an embodiment, the self-referential indicator involves a comparison of the process parameter value to at least an average of measured values of the process parameter. In an embodiment, the self-referential indicator involves a comparison of the process parameter value to a combination of an average of measured values of the process parameter and three times the standard deviation of the measured values of the process parameter. In an embodiment, the method further comprises evaluating the plurality of substrate measurement recipes against target sigma and the selected one or more substrate measurement recipes have a value of the target sigma that meets or crosses a threshold.

In an embodiment, there is provided a method comprising: evaluating a plurality of substrate measurement recipes for measurement of a metrology target on a substrate processed using a patterning process, against a stack difference parameter, the stack difference parameter representing an un-designed difference in physical configuration between adjacent periodic structures of the metrology target or between the metrology target and another adjacent target on the substrate; and selecting one or more substrate measurement recipes from the plurality of substrate measurement recipes that have the stack difference parameter that meets or crosses a threshold.

In an embodiment, the stack difference parameter comprises a periodic structure intensity imbalance. In an embodiment, the periodic structure intensity imbalance is a function of (i) the difference between the average intensity of measurement radiation from a first adjacent periodic structure or target and the average intensity of measurement radiation from a second adjacent periodic structure or target, and (ii) the addition of an average intensity of measurement radiation from the first adjacent periodic structure or target with an average intensity of measurement radiation from the second adjacent periodic structure or target. In an embodiment, the average intensity of measurement radiation from the first adjacent periodic structure or target corresponds to −n order radiation and the average intensity of measurement radiation from the second adjacent periodic structure or target corresponds to −n order radiation, wherein n is an integer greater than or equal to 1. In an embodiment, the method further comprises evaluating the plurality of substrate measurement recipes against stack sensitivity and the selected one or more substrate measurement recipes have a value of the stack sensitivity that meets or crosses a threshold. In an embodiment, the method further comprises evaluating the plurality of substrate measurement recipes against overlay sensitivity and the selected one or more substrate measurement recipes have a value of the overlay sensitivity within a certain finite range from a maximum or minimum value of the overlay sensitivity. In an embodiment, the method further comprises evaluating the plurality of substrate measurement recipes against target sigma and the selected one or more substrate measurement recipes have a value of the target sigma that meets or crosses a threshold. In an embodiment, the method further comprises evaluating the plurality of substrate measurement recipes against a robustness indicator representing statistical variation of a sensitivity parameter across the substrate, and the selected one or more substrate measurement recipes have a value of the robustness indicator that meets or crosses a threshold. In an embodiment, the robustness indicator represents a statistical variation of overlay sensitivity across the substrate divided by the average of absolute values of overlay sensitivity across the substrate. In an embodiment, the method further comprises evaluating the plurality of substrate measurement recipes against a self-referential indicator that involves a process parameter value determined from a fitting among asymmetry data for a first periodic structure against asymmetry data for a second periodic structure, and the selected one or more substrate measurement recipes have a value of the self-referential indicator that meets or crosses a threshold. In an embodiment, the self-referential indicator involves a comparison of the process parameter value to at least an average of measured values of the process parameter. In an embodiment, the self-referential indicator involves a comparison of the process parameter value to a combination of an average of measured values of the process parameter and three times the standard deviation of the measured values of the process parameter.

While the embodiments disclosed above are described in terms of diffraction based overlay measurements (e.g., measurements made using the second measurement branch of the apparatus shown in FIG. 7A), in principle the same models can be used for pupil based overlay measurements (e.g., measurements made using the first measurement branch of the apparatus shown in FIG. 7A). Consequently, it should be appreciated that the concepts described herein are equally applicable to diffraction based overlay measurements and pupil based overlay measurements.

While embodiments of the metrology target and process parameters described herein have mostly been described in the terms of an overlay target used to measure overlay, embodiments of the metrology target described herein may be used to measure one or more additional or alternative patterning process parameters. For example, the metrology target may be used to measure exposure dose variation, measure exposure focus/defocus, measure CD, etc. Further, the description here may also apply, with modifications as appropriate, to, e.g., substrate and/or patterning device alignment in a lithographic apparatus using an alignment mark. Similarly, the appropriate recipe for the alignment measurement may be determined.

So, while a performance parameter of interest is overlay, other parameters (e.g., dose, focus, CD, etc.) of performance of the patterning process can be determined using the methods described herein. The performance parameter (e.g., overlay, CD, focus, dose, etc.) can be fed back (or fed forward) for improvement of the patterning process, improvement of the target, and/or used to improve the modeling, measurement and calculation processes described herein.

While the target structures described above are metrology targets specifically designed and formed for the purposes of measurement, in other embodiments, properties may be measured on targets which are functional parts of devices formed on the substrate. Many devices have regular, periodic structures akin to a grating. The term "target", "grating" or "periodic structure" of a target as used herein does not require that the applicable structure has been provided specifically for the measurement being performed. Further, pitch P of the metrology target is close to the resolution limit of the optical system of the measurement tool, but may be much larger than the dimension of typical product features made by a patterning process in the target portions C. In practice the features and/or spaces of the periodic structures may be made to include smaller structures similar in dimension to the product features.

In association with the physical structures of the targets as realized on substrates and patterning devices, an embodiment may include a computer program containing one or more sequences of machine-readable instructions and/or functional data describing the target design, describing a method of designing a target for a substrate, describing a method of producing a target on a substrate, describing a method of measuring a target on a substrate and/or describing a method of analyzing a measurement to obtain information about a patterning process. This computer program may be executed for example within unit PU in the apparatus of FIG. 7 and/or the control unit LACU of FIG. 2. There may also be provided a data storage medium (e.g., semiconductor memory, magnetic or optical disk) having such a computer program stored therein. Where an existing inspection apparatus, for example of the type shown in FIG. 7, is already in production and/or in use, an embodiment can be implemented by the provision of an updated computer program product for causing a processor to perform one or more of the methods described herein. The program may optionally be arranged to control the optical system, substrate support and the like to perform a method of measuring a parameter of the patterning process on a suitable plurality of targets. The program can update the lithographic and/or metrology recipe for measurement of further substrates. The program may be arranged to control (directly or indirectly) the lithographic apparatus for the patterning and processing of further substrates.

Further, embodiments have been described herein in relation to diffraction-based metrology, which, for example, measures the relative position of overlapping periodic structures from the intensity from the diffracted orders. However, embodiments herein may be applied, with appropriate modification where needed, to image-based metrology, which, for example, measures the relative position from target 1 in layer 1 to target 2 in layer 2 using high-quality images of the targets. Usually these targets are periodic structures or "boxes" (Box-in-Box (BiB)).

The term "optimizing" and "optimization" as used herein refers to or means adjusting an apparatus and/or process of the patterning process, which may include adjusting a lithography process or apparatus, or adjusting the metrology process or apparatus (e.g., the target, measurement tool, etc.), such that a figure of merit has a more desirable value, such as measurement, patterning and/or device fabrication results and/or processes have one or more desirable characteristics, projection of a design layout on a substrate being more accurate, a process window being larger, etc. Thus, optimizing and optimization refers to or means a process that identifies one or more values for one or more design variables that provide an improvement, e.g. a local optimum, in a figure of merit, compared to an initial set of values of the design variables. "Optimum" and other related terms should be construed accordingly. In an embodiment, optimization steps can be applied iteratively to provide further improvements in one or more figures of merit.

In the face of distinguishing intensity values due to structural asymmetry alone, a structure, formed by a single grating for example, placed in close proximity with a metrology target, such as a target used to provide overlay values, is found to provide beneficial corrections. The structural asymmetry only structure, for example gratings present in only L1 in FIG. 11, thus no top-gratings as depicted in L2 of FIG. 11, is measured at the same time with the metrology target, as both have dimensions suitable to allow inclusion in a measurement spot. Detecting the intensity asymmetry originating from the structural asymmetry only structure (the metrology target provides intensity values comprising both structural asymmetry and overlay error or asymmetry) allows a correction of the overlay values obtained from the metrology target.

An advantageous method to monitor the contribution of intensity originating from structural asymmetry related scattering is comprising detecting simultaneously the intensity scattered from a metrology target comprising overlapping gratings and the intensity scattered from a structural asymmetry only target, calculating a value proportional to the intensity scattered by structural asymmetry wherein the calculation is an addition of intensity scattered by corresponding diffraction orders.

A value proportional to the intensity scattered by a structural asymmetry structure, such as a target comprising only a bottom grating, wherein the value is obtained by the addition of the intensity scattered by corresponding diffraction orders, provides further advantages in calibration and correction of the overlay metrology setup, in providing estimations in relation to the accuracy of the overlay metrology, in providing further estimations in relation to other parameter of interest of the lithographic process, for example process changes in the lithographic steps within the lithographic facility.

A further advantage of using a value proportional to the summation of the intensity of corresponding diffraction orders is the calculation of a proportionality factor which provides the intensity values, as originating from a structural asymmetry only target, in "nm" values. Such translation is beneficial to compare, monitor and correct the lithographic process, or the metrology recipe setup, or the metrology process itself.

An embodiment of the invention may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

One or more aspects disclosed herein may be implemented in a control system. Any control system described herein may each or in combination be operable when the one or more computer programs are read by one or more computer processors located within at least one component of an apparatus. The control systems may each or in combination have any suitable configuration for receiving, processing, and sending signals. One or more processors are configured to communicate with the at least one of the control systems. For example, each control system may include one or more processors for executing the computer programs that include machine-readable instructions for the methods described above. The control systems may include data storage medium for storing such computer programs, and/or hardware to receive such medium. So the control system(s) may operate according the machine readable instructions of one or more computer programs.

Although specific reference may have been made above to the use of embodiments in the context of optical lithography, it will be appreciated that embodiments of the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method comprising:
evaluating a plurality of substrate measurement recipes for measurement of a metrology target processed using a patterning process, against stack sensitivity and overlay sensitivity, each of the substrate measurement recipes having a different set of one or more values for one or more parameters that relate to the measurement itself; and
selecting one or more substrate measurement recipes from the plurality of substrate measurement recipes that have a value of the stack sensitivity that meets or crosses a threshold and that have a value of the overlay sensitivity within a certain finite range from a maximum or minimum value of the overlay sensitivity.

2. The method of claim 1, further comprising evaluating the plurality of substrate measurement recipes against target sigma and the selected one or more substrate measurement recipes have a value of the target sigma that meets or crosses a threshold.

3. The method of claim 1, further comprising evaluating the plurality of substrate measurement recipes against a robustness indicator representing statistical variation of a sensitivity parameter across the substrate, and the selected one or more substrate measurement recipes have a value of the robustness indicator that meets or crosses a threshold.

4. The method of claim 1, further comprising evaluating the plurality of substrate measurement recipes against a stack difference parameter, the stack difference parameter representing an un-designed difference in physical configuration between adjacent periodic structures of the metrology target or between the metrology target and another adjacent target on the substrate, and the selected one or more substrate measurement recipes have a value of the stack difference parameter that meets or crosses a threshold.

5. The method of claim 4, wherein the stack difference parameter comprises a periodic structure intensity imbalance.

6. The method of claim 1, further comprising evaluating the plurality of substrate measurement recipes against a self-referential indicator that involves a process parameter value determined from a fitting among asymmetry data for a first periodic structure against asymmetry data for a second periodic structure, and the selected one or more substrate measurement recipes have a value of the self-referential indicator that meets or crosses a threshold.

7. The method of claim 1, wherein the evaluating comprises computing a multi-variable cost function, the multi-variable cost function representing a metric characterizing the stack sensitivity and the overlay sensitivity, the metric being a function of a plurality of parameters from the substrate measurement recipe; and adjusting one or more of the parameters and computing the cost function with the adjusted one or more design parameters, until a certain termination condition is satisfied.

8. A method comprising:
evaluating a plurality of substrate measurement recipes for measurement of a metrology target on a substrate processed using a patterning process, against a robustness indicator representing statistical variation of a sensitivity parameter across the substrate, each of the substrate measurement recipes having a different set of one or more values for one or more parameters that relate to the measurement itself; and
selecting one or more substrate measurement recipes from the plurality of substrate measurement recipes that have the robustness indicator that meets or crosses a threshold.

9. The method of claim 8, wherein the robustness indicator represents a statistical variation of overlay sensitivity across the substrate divided by the average of absolute values of overlay sensitivity across the substrate.

10. The method of claim 8, further comprising evaluating the plurality of substrate measurement recipes against stack sensitivity and the selected one or more substrate measurement recipes have a value of the stack sensitivity that meets or crosses a threshold.

11. The method of claim 8, further comprising evaluating the plurality of substrate measurement recipes against overlay sensitivity and the selected one or more substrate measurement recipes have a value of the overlay sensitivity within a certain finite range from a maximum or minimum value of the overlay sensitivity.

12. The method of claim 8, further comprising evaluating the plurality of substrate measurement recipes against a stack difference parameter, the stack difference parameter representing an un-designed difference in physical configuration between adjacent periodic structures of the metrology target or between the metrology target and another adjacent target on the substrate, and the selected one or more substrate measurement recipes have a value of the stack difference parameter that meets or crosses a threshold.

13. The method of claim 8, further comprising evaluating the plurality of substrate measurement recipes against a self-referential indicator that involves a process parameter value determined from a fitting among asymmetry data for a first periodic structure against asymmetry data for a second periodic structure, and the selected one or more substrate measurement recipes have a value of the self-referential indicator that meets or crosses a threshold.

14. The method of claim 8, further comprising evaluating the plurality of substrate measurement recipes against target sigma and the selected one or more substrate measurement recipes have a value of the target sigma that meets or crosses a threshold.

15. A method comprising:
evaluating a plurality of substrate measurement recipes for measurement of a metrology target on a substrate processed using a patterning process, against a stack difference parameter, the stack difference parameter representing an un-designed difference in physical configuration between adjacent periodic structures of the metrology target or between the metrology target and another adjacent target on the substrate, each of the substrate measurement recipes having a different set of one or more values for one or more parameters that relate to the measurement itself; and
selecting one or more substrate measurement recipes from the plurality of substrate measurement recipes that have the stack difference parameter that meets or crosses a threshold.

16. The method of claim 15, wherein the stack difference parameter comprises a periodic structure intensity imbalance.

17. The method of claim 15, further comprising evaluating the plurality of substrate measurement recipes against stack sensitivity and the selected one or more substrate measurement recipes have a value of the stack sensitivity that meets or crosses a threshold.

18. The method of claim 15, further comprising evaluating the plurality of substrate measurement recipes against overlay sensitivity and the selected one or more substrate measurement recipes have a value of the overlay sensitivity within a certain finite range from a maximum or minimum value of the overlay sensitivity.

19. The method of claim 15, further comprising evaluating the plurality of substrate measurement recipes against target sigma and the selected one or more substrate measurement recipes have a value of the target sigma that meets or crosses a threshold.

20. The method of claim 15, further comprising evaluating the plurality of substrate measurement recipes against a robustness indicator representing statistical variation of a sensitivity parameter across the substrate, and the selected one or more substrate measurement recipes have a value of the robustness indicator that meets or crosses a threshold.

21. The method of claim 15, further comprising evaluating the plurality of substrate measurement recipes against a self-referential indicator that involves a process parameter value determined from a fitting among asymmetry data for a first periodic structure against asymmetry data for a second periodic structure, and the selected one or more substrate measurement recipes have a value of the self-referential indicator that meets or crosses a threshold.

22. A non-transitory computer program product comprising machine-readable instructions, the instructions configured, upon execution by a computer system, configured to cause the computer system to at least:

evaluate a plurality of substrate measurement recipes for measurement of a metrology target processed using a patterning process, against stack sensitivity and overlay sensitivity, each of the substrate measurement recipes having a different set of one or more values for one or more parameters that relate to the measurement itself; and select one or more substrate measurement recipes from the plurality of substrate measurement recipes that have a value of the stack sensitivity that meets or crosses a threshold and that have a value of the overlay sensitivity within a certain finite range from a maximum or minimum value of the overlay sensitivity.

23. A non-transitory computer program product comprising machine-readable instructions, the instructions configured, upon execution by a computer system, configured to cause the computer system to at least:

evaluate a plurality of substrate measurement recipes for measurement of a metrology target on a substrate processed using a patterning process, against a robustness indicator representing statistical variation of a sensitivity parameter across the substrate, each of the substrate measurement recipes having a different set of one or more values for one or more parameters that relate to the measurement itself; and select one or more substrate measurement recipes from the plurality of substrate measurement recipes that have the robustness indicator that meets or crosses a threshold.

24. A non-transitory computer program product comprising machine-readable instructions, the instructions configured, upon execution by a computer system, configured to cause the computer system to at least:

evaluate a plurality of substrate measurement recipes for measurement of a metrology target on a substrate processed using a patterning process, against a stack difference parameter, the stack difference parameter representing an un-designed difference in physical configuration between adjacent periodic structures of the metrology target or between the metrology target and another adjacent target on the substrate, each of the substrate measurement recipes having a different set of one or more values for one or more parameters that relate to the measurement itself; and select one or more substrate measurement recipes from the plurality of substrate measurement recipes that have the stack difference parameter that meets or crosses a threshold.

* * * * *